United States Patent
Beall

(10) Patent No.: US 7,531,628 B2
(45) Date of Patent: May 12, 2009

(54) CANINE CD20 COMPOSITIONS

(75) Inventor: Melissa J. Beall, Cape Elizabeth, ME (US)

(73) Assignee: IDEXX Laboratories, Inc., Westbrook, ME (US)

(*) Notice: Subject to any disclaimer, the term of this patent is extended or adjusted under 35 U.S.C. 154(b) by 373 days.

(21) Appl. No.: 11/138,949

(22) Filed: May 26, 2005

(65) Prior Publication Data

US 2005/0271662 A1 Dec. 8, 2005

Related U.S. Application Data

(60) Provisional application No. 60/575,172, filed on May 28, 2004.

(51) Int. Cl.
*C07K 14/00* (2006.01)
*C07K 5/00* (2006.01)

(52) U.S. Cl. ............ 530/350; 530/300; 530/352; 435/69.1; 435/69.7

(58) Field of Classification Search .......... None
See application file for complete search history.

(56) References Cited

U.S. PATENT DOCUMENTS

| | | | |
|---|---|---|---|
| 5,849,898 A | 12/1998 | Seed et al. | |
| 2003/0129696 A1 | 7/2003 | Ni et al. | |
| 2005/0048071 A1 | 3/2005 | Bae | |
| 2005/0238650 A1 | 10/2005 | Crowley et al. | |

FOREIGN PATENT DOCUMENTS

WO 105075640 8/2005

OTHER PUBLICATIONS

Polyak et al., Blood, 2002, 99(9):3256-3262.*
International Search Report for corresponding PCT application serial No. PCT/US2005/018515 dated May 17, 2006.
Coyle, et al., "Characterization of Lymphocytes in Canine Gastrointestinal Lymphoma", Vet. Pathol. 41:141-146 (2004).
Stamenkovic, et al., "Analysis of Two cDNA Clones Encoding the B Lymphocyte Antigen CD20) (B1, Bp35), a Type III Integral Membrane Protein", J. Exp. Med. vol. 167, p. 1975-1980 (1988).
Rastetter, et al., "Rituximab: Expanding Role in Therapy for Lymphomas and Autoimmune Diseases", Annu. Rev. Med. 55:477-503 (2004).
Jubala, et al., "CD20 Expression in Normal Canine B Cells and in Canine non-Hodgkin Lymphoma", Vet Pathol. 42:468-476 (2005).
Kano, et al., "Canine CD20 Gene", Veterinary Immunology and Immunopathology, 108, p. 265-268 (2005).
English translation of Japanese Patent No. PCT/JP2005/001880; International Publication No. WO 2005/075640 A1, filing date Feb. 9, 2005.
Kano, et al., "Canine CD20 Gene", Vet. Immunol. Immunopathol. 108:265-268 (2005).
Ohano, et al., UniProt KB/Trembl Accession No. Q5R1M8, Jul. 24, 2007.
Moore, et al., UniProtKB/Trembl Accession No. Q17QX1, Jul. 24, 2007.
Stemenkovic, et al., "Analysis of two cDNA clones encoding the B lymphocyte antigen CD20 (B1, Bp35), a type III integral emebrane protein", J. Exp. Med. 167:1975-1980 (1988).
Tedder, et al., "Isolation and structure of a cDNA encdoding the B1 (CD20) cell-surface antigen of human B lymphocytes", Proc. natl. Acad. Sci. USA 85:208-212 (1988).
Einfeld, et al., "Molecular cloning of the human B cell CD20 receptor predicts a hydrophobic protein with multiple transmembrane domains", EMBO J. 7:711-717 (1988).
Tedder, et al., "Structure of the gene encoding the human B lymphocyte differentiation antigen CD20 (B1)" J. Immunol. 142:2560-2568 (1989).
The MGC Project Team, "The status, quality, and expansion of the NIH full-length cDNA project: the Mammalian Gene Collection (MCG)", Genome Res. 14:2121-2127 (2004).
Wakamatsu, et al., UniProtKB/Trembl Accession No. A8K83, Dec. 4, 2007.
Taylor, et al., "Human chromosome 11 DNA sequence and analysis including novel gene identification", Nature 440:497-500 (2006).
Letter to Conan Deady, Vice President General Counsel and Secretary of IDEXX Laboratories from Steve P. Hassid from Greenberg Traurig dated Feb. 4, 2008 enclosing prior art.

* cited by examiner

*Primary Examiner*—Elizabeth C. Kemmerer
*Assistant Examiner*—Xiaozhen Xie
(74) *Attorney, Agent, or Firm*—McDonnell Boehnen Hulbert & Berghoff LLP

(57) ABSTRACT

The invention provides canine CD20 nucleotide and protein sequences. These compositions are useful in the diagnosis and treatment of, e.g., CD20+ B-cell lymphoma, immune-mediated hemolytic anemia, immune-mediated thrombocytopenia, and systemic lupus erythematosus (SLE) in canines and felines.

5 Claims, 12 Drawing Sheets

FIG. 1

Nucleotide sequence for the portion of canine CD20 initially amplified from cDNA
(SEQ ID NO: 1)

```
1    GCGCTCTTTG CTGCCATTTC TGGAATAATT TTTTTGATCA TGGACATATT TAATATTACC
61   ATTTCCCATT TTTTAAAAAT GGAGAATTTG AATCTTATTA AAGCTCCCAT ACCATATGTT
121  GACATACACA ACTGTGACCC AGCTAACCCC TCTGAGAAAA ACTCTTTATC TATACAATAT
181  TGTGGCAGCA TACGATCTGT TTTCTTGGGC GTTTTTGCTG TGATGCTGAT CTTTGCCTTC
241  TTCCAGC
```

FIG. 2

Polypeptide sequence for a portion of canine CD20 translated from SEQ ID NO: 1
aligned with a comparable region of human and mouse CD20.

```
XSLSLFAAISGIILSIMDILNITISHFLKMEXLNLIXAXXPYVDIYNCEPANPSEKNSPS
-----+---------+---------+---------+---------+---------+-
     130       140       150       160       170       180
-----+---------+---------+---------+---------+---------+-
NSLSLFAAISGMILSIMDILNIKISHFLKMESLNFIRAHTPYINIYNCEPANPSEKNSPS  Human CD20
SSLSLFAAISGIILSIMDILNMTLSHFLKMRRLELIQTSKPYVDIYDCEPSNSSEKNSPS  Mouse CD20
---ALFAAISGIIFLIMDIFNITISHFLKMENLNLIKAPIPYVDIHNCDPANPSEKNSLS  Canine CD20

TQYCXSIQSVFLGILSVMLIFAFFQXLVXAGIVENEWKRXCXRXKSNXVLLSAXEKXEQT
-----+---------+---------+---------+---------+---------+-
     190       200       210       220       230       240
-----+---------+---------+---------+---------+---------+-
TQYCYSIQSLFLGILSVMLIFAFFQELVIAGIVENEWKRTCSRPKSNIVLLSAEEKKEQT  Human CD20
TQYCNSIQSVFLGILSAMLISAFFQKLVTAGIVENEWKRMCTRSKSNVVLLSAGEKNEQT  Mouse CD20
IQYCGSIRSVFLGVPAVMLIFAFFQ                                     Canine CD20
```

Human CD 20 (Accesssion #A30586): SEQ ID NO:2
Mouse CD 20 (Accession #AAA37394): SEQ ID NO:3
Canine CD 20: SEQ ID NO:4

FIG. 3

Canine CD20 Nucleotide Sequence SEQ ID NO: 5

```
  1 GGGACTAGCA CTGGAAGTGA ACTCAGCAGC GAACAACTGA ATCAGCCACT CGCCCTAAGG
 61 CCACAGACAC TCAGGAGTTC AGAGGGTGAG ATGACAACAC CCAGAAATTC AATGAGTGGA
121 ACTCTCCCGG TAGATCCTAT GAAAAGCCCT ACTGCCATGT ATCCTGTTCA AAAAATAATT
181 CCCAAAAGGA TGCCTTCAGT GGTGGGCCCT ACACAAAACT TCTTCATGAG GGAATCTAAG
241 ACACTGGGGG CTGTCCAGAT TATGAATGGG CTCTTCCACA TTGCCCTAGG CAGCCTCCTG
301 ATGATTCACA CGGATGTCTA TGCGCCCATC TGTATAACTA TGTGGTACCC TCTCTGGGGA
361 GGCATTATGT TCATCATTTC TGGATCACTC CTGGCAGCAG CGGACAAAAA CCCCAGGAAG
421 AGTTTGGTCA AAGGAAAAAT GATAATGAAC TCATTGAGCC TCTTTGCTGC CATTTCTGGA
481 ATAATTTTTT TGATCATGGA CATATTTAAT ATTACCATTT CCCATTTTTT AAAAATGGAG
541 AATTTGAATC TTATTAAAGC TCCCATACCA TATGTTGACA TACACAACTG TGACCCAGCT
601 AACCCCTCTG AGAAAAACTC TTTATCTATA CAATATTGTG GCAGCATACG ATCTGTTTTC
661 TTGGGCGTTT TTGCTGTGAT GGTGATCTTT ACCTTTTTCC AGAAACTTGT GACAGCTGGC
721 ATTGTTGAGA ATGAATGGAA AAAACTGTGC TCTAAACCTA AATCTGATGT AGTTGTTCTG
781 TTAGCTGCTG AAGAAAAAAA AGAACAGCCG ATTGAAACAA CAGAAGAAAT GGTTGAGCTG
841 ACTGAAATAG CTTCCCAACC AAAGAAAGAA GAAGACATTG AAATTATTCC AGTCCAAGAA
901 GAAGAAGAGG AACTGGAAAT AAACTTTGCA GAACCTCCCC AGGAGCAGGA ATCTTCACCA
961 ATAGAAAACG ACAGCATCCC TTAA
```

FIG. 4

Canine CD20 Protein Sequence SEQ ID NO: 6

```
  1    MTTPRNSMSG TLPVDPMKSP TAMYPVQKII PKRMPSVVGP TQNFFMRESK TLGAVQIMNG
 61    LFHIALGSLL MIHTDVYAPI CITMWYPLWG GIMFIISGSL LAAADKNPRK SLVKGKMIMN
121    SLSLFAAISG IIFLIMDIFN ITISHFLKME NLNLIKAPIP YVDIHNCDPA NPSEKNSLSI
181    QYCGSIRSVF LGVFAVMVIF TFFQKLVTAG IVENEWKKLC SKPKSDVVVL LAAEEKKEQP
241    IETTEEMVEL TEIASQPKKE EDIEIIPVQE EEEELEINFA EPPQEQESSP IENDSIP
```

FIG. 5

Alignment of human, mouse, feline and canine CD20 amino acid sequences.

```
                          1                                                           60
         A30586_human_CD20 MTTPRNSVNGTFPAEPMKGPIAMQSGPKPLFRRMSSLVGPTQSFFMRESKTLGAVQIMNG
        AAA37394_murine_CD20 .......MSGPFPAEPTKGPLAMQPAPKVNLKRTSSLVGPTQSFFMRESKALGAVQIMNG
        BAD77809_Feline_CD20 MTTPRNSMSGTLPADAMKSPTAMNPVQKIIPKKMPSVVGPTQNFFMKESKPLGAVQIMNG
    Ca_CD20_contig_translated MTTPRNSMSGTLPVDPMKSPTAMYPVQKIIPKRMPSVVGPTQNFFMRESKTLGAVQIMNG 61                                                          120
         A30586_human_CD20 LFHIALGGLLMIPAGIYAPICVTVWYPLWGGIMYIISGSLLAAT.EKNSRKCLVKGKMIM
        AAA37394_murine_CD20 LFHITLGGLLMIPTGVFAPICLSVWYPLWGGIMYIISGSLLAAAAEKTSRKSLVKAKVIM
        BAD77809_Feline_CD20 LFHMALGGLLMTHMFVYAPTCMTVWYPLWGGTMYTISGSLLVAA.FKNPRKSLVKGKMIM
    Ca_CD20_contig_translated LFHIALGSLLMIHTDVYAPICITMWYPLWGGIMFIISGSLLAAA.DKNPRKSLVKGKMIM 121                                                         180
         A30586_human_CD20 NSLSLFAAISGMILSIMDILNIKISHFLKMESLNFIRAHTPYINIYNCEP.ANPSEKNSP
        AAA37394_murine_CD20 SSLSLFAAISGIILSIMDILNMTLSHFLKMRRLELIQTSKPYVDIYDCEP.SNSSEKNSP
        BAD77809_Feline_CD20 NSLSLFAAISGMILLIMDIFNIAISHFFKMENLNLLKSPKPYIDITCQPESKPSEKNSL
    Ca_CD20_contig_translated NSLSLFAAISGIIFLIMDIFNITISHFLKMENLNLIKAPIPYVDIHNCDP.ANPSEKNSL 181                                                         240
         A30586_human_CD20 STQYCYSIQSLFLGILSVMLIFAFFQELVIAGIVENEWKRTCSRPKSN.IVLLSAEEKKE
        AAA37394_murine_CD20 STQYCNSIQSVFLGILSAMLISAFFQKLVTAGIVENEWKRMCTRSKSN.VVLLSAGEKNE
        BAD77809_Feline_CD20 SIKYCDSIRSVFLSIFAVMVVFTLFQKLVTAGIVENEWKKLCSKPKADVVVLLAAEEKKE
    Ca_CD20_contig_translated SIQYCGSIRSVFLGVFAVMVIFTFFQKLVTAGIVENEWKKLCSKPKSDVVVLLAAEEKKE 241                                                         300
         A30586_human_CD20 QTIEIKEEVVGLTETSSQPKNEEDIEIIPIQEEEEEETETNFPEPPQDQESSPIENDSSP
        AAA37394_murine_CD20 QTIKMKEEIIELSGVSSQPKNEEEIEIIPVQEEEEEEAEINFPAPPQEQESLPVENEIAP
        BAD77809_Feline_CD20 QLVEITEEAVELTEVSSQPKNEEDIEIIPVQEEEEE.TEMNFPEPPQDQEPSLIENDSIP
    Ca_CD20_contig_translated QPIETTEEMVELTEIASQPKKEEDIEIIPVQEEEEE.LEINFAEPPQEQESSPIENDSIP
```

A30586 Human CD20 (SEQ ID NO:7); extracellular domain in grey (SEQ ID NO:12)
AAA37395 Murine CD20 (SEQ ID NO:8); extracellular domain in grey (SEQ ID NO:13)
BAD77809 Feline CD20 (SEQ ID NO: 9); extracellular domain in grey (SEQ ID NO:14)
Canine CD20 (SEQ ID NO:6); extracellular domain in grey (SEQ ID NO:10)

Expression of canine CD20 in COS7 cells and evaluation on Western Blot.

Expression of canine CD20 in COS7 cells and evaluation by immunofluoresence.

FIG. 8

CD20 extracellular domain peptide (53-mer): (SEQ ID NO:10)

DIFNITISHFLKMENLNLIKAPIPYVDIHNCDPANPSEKNSLSIQYCGSIRSV

CD20 extracellular domain peptide with T-cell epitope (75-mer): (SEQ ID NO:11)

DDLQAVHAAHAEINEADHIDIDDIFNITISHFLKMENLNLIKAPIPYVDIHNCDPANPSEKNSLSIQYCGSIRSV

Serum titers for mice immunized with canine CD20 using the peptide ELISA.

Coomassie stained gel of three purified IgM monoclonal antibodies to canine CD20.

Flow cytometry results for the four IgM monoclonal antibodies to canine CD20 using lymph node aspirates from dogs with lymphoma.

Flow cytometry results for IgM monoclonal antibody F7A5 in a dog with B-cell lymphoma.

FIG. 13
Identification of B-lymphocytes using the F7A5 monoclonal antibody to the extracellular domain of canine CD20 in a point of care hematology instrument.
A. Small lymphocytes
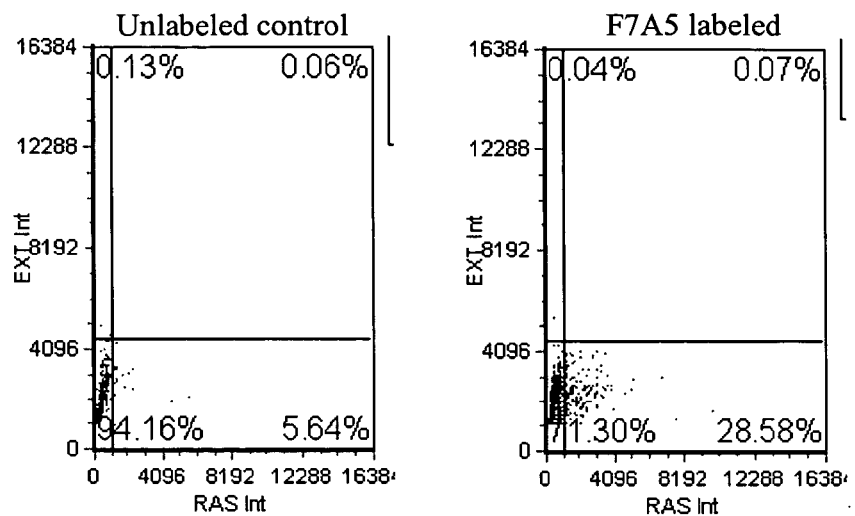
B. Medium lymphocytes
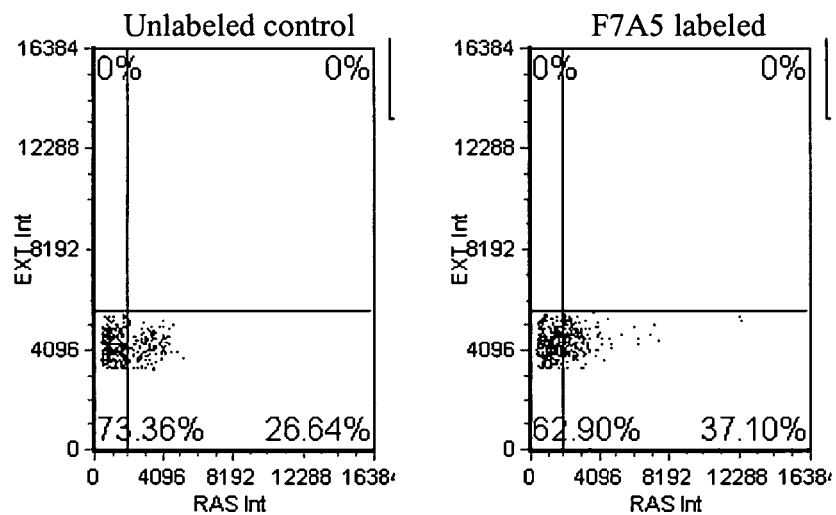

Identification of B-lymphhocytes in a lymph node aspirate from a cat with lymphoma using monoclonal antibody F7A5 and a point of care hematology instrument.

SEQUENCE LISTING

<160> NUMBER OF SEQ ID NOS: 14

<210> SEQ ID NO 1
<211> LENGTH: 247
<212> TYPE: DNA
<213> ORGANISM: Canis familiaris

<400> SEQUENCE: 1

```
gcgctctttg ctgccatttc tggaataatt tttttgatca tggacatatt taatattacc      60
atttcccatt ttttaaaaat ggagaatttg aatcttatta aagctcccat accatatgtt     120
gacatacaca actgtgaccc agctaacccc tctgagaaaa actctttatc tatacaatat     180
tgtggcagca tacgatctgt tttcttgggc gttttgctg tgatgctgat ctttgccttc      240
ttccagc                                                               247
```

<210> SEQ ID NO 2
<211> LENGTH: 120
<212> TYPE: PRT
<213> ORGANISM: Homo sapiens

<400> SEQUENCE: 2

Asn Ser Leu Ser Leu Phe Ala Ala Ile Ser Gly Met Ile Leu Ser Ile
1               5                   10                  15

Met Asp Ile Leu Asn Ile Lys Ile Ser His Phe Leu Lys Met Glu Ser
            20                  25                  30

Leu Asn Phe Ile Arg Ala His Thr Pro Tyr Ile Asn Ile Tyr Asn Cys
        35                  40                  45

Glu Pro Ala Asn Pro Ser Glu Lys Asn Ser Pro Ser Thr Gln Tyr Cys
    50                  55                  60

Tyr Ser Ile Gln Ser Leu Phe Leu Gly Ile Leu Ser Val Met Leu Ile
65                  70                  75                  80

Phe Ala Phe Phe Gln Glu Leu Val Ile Ala Gly Ile Val Glu Asn Glu
                85                  90                  95

Trp Lys Arg Thr Cys Ser Arg Pro Lys Ser Asn Ile Val Leu Leu Ser
            100                 105                 110

Ala Glu Glu Lys Lys Glu Gln Thr
        115                 120

<210> SEQ ID NO 3
<211> LENGTH: 120
<212> TYPE: PRT
<213> ORGANISM: Mus musculus

<400> SEQUENCE: 3

Ser Ser Leu Ser Leu Phe Ala Ala Ile Ser Gly Ile Ile Leu Ser Ile
1               5                   10                  15

Met Asp Ile Leu Asn Met Thr Leu Ser His Phe Leu Lys Met Arg Arg
            20                  25                  30

Leu Glu Leu Ile Gln Thr Ser Lys Pro Tyr Val Asp Ile Tyr Asp Cys
        35                  40                  45

Glu Pro Ser Asn Ser Ser Glu Lys Asn Ser Pro Ser Thr Gln Tyr Cys
    50                  55                  60

Asn Ser Ile Gln Ser Val Phe Leu Gly Ile Leu Ser Ala Met Leu Ile
65                  70                  75                  80

Ser Ala Phe Phe Gln Lys Leu Val Thr Ala Gly Ile Val Glu Asn Glu
                85                  90                  95

Trp Lys Arg Met Cys Thr Arg Ser Lys Ser Asn Val Val Leu Leu Ser
            100                 105                 110

Ala Gly Glu Lys Asn Glu Gln Thr
        115                 120

<210> SEQ ID NO 4
<211> LENGTH: 82
<212> TYPE: PRT
<213> ORGANISM: Canis familiaris

<400> SEQUENCE: 4

Ala Leu Phe Ala Ala Ile Ser Gly Ile Ile Phe Leu Ile Met Asp Ile
1               5                   10                  15

Phe Asn Ile Thr Ile Ser His Phe Leu Lys Met Glu Asn Leu Asn Leu
            20                  25                  30

Ile Lys Ala Pro Ile Pro Tyr Val Asp Ile His Asn Cys Asp Pro Ala
        35                  40                  45

Asn Pro Ser Glu Lys Asn Ser Leu Ser Ile Gln Tyr Cys Gly Ser Ile
    50                  55                  60

Arg Ser Val Phe Leu Gly Val Phe Ala Val Met Leu Ile Phe Ala Phe
65                  70                  75                  80

Phe Gln

<210> SEQ ID NO 5
<211> LENGTH: 984
<212> TYPE: DNA
<213> ORGANISM: Canis familiaris

<400> SEQUENCE: 5
gggactagca ctggaagtga actcagcagc gaacaactga atcagccact cgccctaagg      60
ccacagacac tcaggagttc agagggtgag atgacaacac ccagaaattc aatgagtgga     120
actctcccgg tagatcctat gaaaagccct actgccatgt atcctgttca aaaataatt     180 cccaaaagga tgccttcagt ggtgggccct acacaaaact tcttcatgag gaatctaag     240 acactggggg ctgtccagat tatgaatggg ctcttccaca ttgccctagg cagcctcctg     300
atgattcaca cggatgtcta tgcgcccatc tgtataacta tgtggtaccc tctctgggga     360
ggcattatgt tcatcatttc tggatcactc ctggcagcag cggacaaaaa ccccaggaag     420
agtttggtca aggaaaaaat gataatgaac tcattgagcc tctttgctgc catttctgga     480
ataatttttt tgatcatgga catatttaat attaccattt cccatttttt aaaaatggag     540
aatttgaatc ttattaaagc tcccatacca tatgttgaca tacacaactg tgacccagct     600 aaccctctg agaaaactc tttatctata caatattgtg gcagcatacg atctgttttc     660
ttgggcgttt tgctgtgat ggtgatcttt acctttttcc agaaacttgt gacagctggc     720
attgttgaga atgaatggaa aaaactgtgc tctaaaccta atctgatgt agttgttctg     780 ttagctgctg aagaaaaaaa agaacagccg attgaaacaa cagaagaaat ggttgagctg     840 actgaaaatag cttcccaacc aaagaaagaa gaagacattg aaattattcc agtccaagaa     900
gaagaagagg aactggaaat aaactttgca gaacctcccc aggagcagga atcttcacca     960
atagaaaacg acagcatccc ttaa                                            984

<210> SEQ ID NO 6
<211> LENGTH: 297
<212> TYPE: PRT
<213> ORGANISM: Canis familiaris

<400> SEQUENCE: 6

Met Thr Thr Pro Arg Asn Ser Met Ser Gly Thr Leu Pro Val Asp Pro
1               5                   10                  15

Met Lys Ser Pro Thr Ala Met Tyr Pro Val Gln Lys Ile Ile Pro Lys
            20                  25                  30

Arg Met Pro Ser Val Val Gly Pro Thr Gln Asn Phe Phe Met Arg Glu
        35                  40                  45

Ser Lys Thr Leu Gly Ala Val Gln Ile Met Asn Gly Leu Phe His Ile
    50                  55                  60

Ala Leu Gly Ser Leu Leu Met Ile His Thr Asp Val Tyr Ala Pro Ile
65                  70                  75                  80

Cys Ile Thr Met Trp Tyr Pro Leu Trp Gly Gly Ile Met Phe Ile Ile
                85                  90                  95

Ser Gly Ser Leu Leu Ala Ala Ala Asp Lys Asn Pro Arg Lys Ser Leu
            100                 105                 110

Val Lys Gly Lys Met Ile Met Asn Ser Leu Ser Leu Phe Ala Ala Ile
        115                 120                 125

Ser Gly Ile Ile Phe Leu Ile Met Asp Ile Phe Asn Ile Thr Ile Ser
    130                 135                 140

His Phe Leu Lys Met Glu Asn Leu Asn Leu Ile Lys Ala Pro Ile Pro
145                 150                 155                 160

Tyr Val Asp Ile His Asn Cys Asp Pro Ala Asn Pro Ser Glu Lys Asn
                165                 170                 175

Ser Leu Ser Ile Gln Tyr Cys Gly Ser Ile Arg Ser Val Phe Leu Gly
            180                 185                 190

Val Phe Ala Val Met Val Ile Phe Thr Phe Phe Gln Lys Leu Val Thr
        195                 200                 205

Ala Gly Ile Val Glu Asn Glu Trp Lys Lys Leu Cys Ser Lys Pro Lys
    210                 215                 220

Ser Asp Val Val Val Leu Leu Ala Ala Glu Glu Lys Lys Glu Gln Pro
225                 230                 235                 240

Ile Glu Thr Thr Glu Glu Met Val Glu Leu Thr Glu Ile Ala Ser Gln
                245                 250                 255

Pro Lys Lys Glu Glu Asp Ile Glu Ile Ile Pro Val Gln Glu Glu Glu
            260                 265                 270

Glu Glu Leu Glu Ile Asn Phe Ala Glu Pro Pro Gln Glu Gln Glu Ser
        275                 280                 285

Ser Pro Ile Glu Asn Asp Ser Ile Pro
    290                 295

<210> SEQ ID NO 7
<211> LENGTH: 297
<212> TYPE: PRT
<213> ORGANISM: Homo sapiens

<400> SEQUENCE: 7

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

```
Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 8
<211> LENGTH: 291
<212> TYPE: PRT
<213> ORGANISM: Mus musculus

<400> SEQUENCE: 8

Met Ser Gly Pro Phe Pro Ala Glu Pro Thr Lys Gly Pro Leu Ala Met
  1               5                  10                  15

Gln Pro Ala Pro Lys Val Asn Leu Lys Arg Thr Ser Ser Leu Val Gly
             20                  25                  30

Pro Thr Gln Ser Phe Phe Met Arg Glu Ser Lys Ala Leu Gly Ala Val
         35                  40                  45

Gln Ile Met Asn Gly Leu Phe His Ile Thr Leu Gly Leu Leu Met
     50                  55                  60

Ile Pro Thr Gly Val Phe Ala Pro Ile Cys Leu Ser Val Trp Tyr Pro
 65                  70                  75                  80

Leu Trp Gly Gly Ile Met Tyr Ile Ile Ser Gly Ser Leu Leu Ala Ala
                 85                  90                  95

Ala Ala Glu Lys Thr Ser Arg Lys Ser Leu Val Lys Ala Lys Val Ile
            100                 105                 110

Met Ser Ser Leu Ser Leu Phe Ala Ala Ile Ser Gly Ile Ile Leu Ser
        115                 120                 125

Ile Met Asp Ile Leu Asn Met Thr Leu Ser His Phe Leu Lys Met Arg
```

```
            130                 135                 140
Arg Leu Glu Leu Ile Gln Thr Ser Lys Pro Tyr Val Asp Ile Tyr Asp
145                 150                 155                 160

Cys Glu Pro Ser Asn Ser Ser Glu Lys Asn Ser Pro Ser Thr Gln Tyr
                165                 170                 175

Cys Asn Ser Ile Gln Ser Val Phe Leu Gly Ile Leu Ser Ala Met Leu
                180                 185                 190

Ile Ser Ala Phe Phe Gln Lys Leu Val Thr Ala Gly Ile Val Glu Asn
                195                 200                 205

Glu Trp Lys Arg Met Cys Thr Arg Ser Lys Ser Asn Val Val Leu Leu
210                 215                 220

Ser Ala Gly Glu Lys Asn Glu Gln Thr Ile Lys Met Lys Glu Glu Ile
225                 230                 235                 240

Ile Glu Leu Ser Gly Val Ser Ser Gln Pro Lys Asn Glu Glu Glu Ile
                245                 250                 255

Glu Ile Ile Pro Val Gln Glu Glu Glu Glu Ala Glu Ile Asn
                260                 265                 270

Phe Pro Ala Pro Pro Gln Glu Gln Glu Ser Leu Pro Val Glu Asn Glu
                275                 280                 285

Ile Ala Pro
    290

<210> SEQ ID NO 9
<211> LENGTH: 298
<212> TYPE: PRT
<213> ORGANISM: Felis catus

<400> SEQUENCE: 9

Met Thr Thr Pro Arg Asn Ser Met Ser Gly Thr Leu Pro Ala Asp Ala
1               5                   10                  15

Met Lys Ser Pro Thr Ala Met Asn Pro Val Gln Lys Ile Ile Pro Lys
                20                  25                  30

Lys Met Pro Ser Val Val Gly Pro Thr Gln Asn Phe Phe Met Lys Glu
                35                  40                  45

Ser Lys Pro Leu Gly Ala Val Gln Ile Met Asn Gly Leu Phe His Met
    50                  55                  60

Ala Leu Gly Gly Leu Leu Met Ile His Met Glu Val Tyr Ala Pro Ile
65                  70                  75                  80

Cys Met Thr Val Trp Tyr Pro Leu Trp Gly Gly Ile Met Tyr Ile Ile
                85                  90                  95

Ser Gly Ser Leu Leu Val Ala Ala Glu Lys Asn Pro Arg Lys Ser Leu
                100                 105                 110

Val Lys Gly Lys Met Ile Met Asn Ser Leu Ser Leu Phe Ala Ala Ile
            115                 120                 125

Ser Gly Met Ile Leu Leu Ile Met Asp Ile Phe Asn Ile Ala Ile Ser
            130                 135                 140

His Phe Phe Lys Met Glu Asn Leu Asn Leu Leu Lys Ser Pro Lys Pro
145                 150                 155                 160

Tyr Ile Asp Ile His Thr Cys Gln Pro Glu Ser Lys Pro Ser Glu Lys
                165                 170                 175

Asn Ser Leu Ser Ile Lys Tyr Cys Asp Ser Ile Arg Ser Val Phe Leu
                180                 185                 190

Ser Ile Phe Ala Val Met Val Val Phe Thr Leu Phe Gln Lys Leu Val
            195                 200                 205
```

-continued

```
Thr Ala Gly Ile Val Glu Asn Glu Trp Lys Lys Leu Cys Ser Lys Pro
    210                 215                 220

Lys Ala Asp Val Val Val Leu Leu Ala Ala Glu Glu Lys Lys Glu Gln
225                 230                 235                 240

Leu Val Glu Ile Thr Glu Glu Ala Val Glu Leu Thr Glu Val Ser Ser
                245                 250                 255

Gln Pro Lys Asn Glu Glu Asp Ile Glu Ile Ile Pro Val Gln Glu Glu
            260                 265                 270

Glu Glu Glu Thr Glu Met Asn Phe Pro Glu Pro Pro Gln Asp Gln Glu
        275                 280                 285

Pro Ser Leu Ile Glu Asn Asp Ser Ile Pro
    290                 295

<210> SEQ ID NO 10
<211> LENGTH: 53
<212> TYPE: PRT
<213> ORGANISM: Canis familiaris

<400> SEQUENCE: 10

Asp Ile Phe Asn Ile Thr Ile Ser His Phe Leu Lys Met Glu Asn Leu
1               5                   10                  15
Asn Leu Ile Lys Ala Pro Ile Pro Tyr Val Asp Ile His Asn Cys Asp
            20                  25                  30

Pro Ala Asn Pro Ser Glu Lys Asn Ser Leu Ser Ile Gln Tyr Cys Gly
        35                  40                  45

Ser Ile Arg Ser Val
    50

<210> SEQ ID NO 11
<211> LENGTH: 75
<212> TYPE: PRT
<213> ORGANISM: Artificial
<220> FEATURE:
<223> OTHER INFORMATION: CD20 extracellular domain peptide with T-cell
      epitope (75-mer)

<400> SEQUENCE: 11

Asp Asp Leu Gln Ala Val His Ala Ala His Ala Glu Ile Asn Glu Ala
1               5                   10                  15

Asp His Ile Asp Ile Asp Asp Ile Phe Asn Ile Thr Ile Ser His Phe
            20                  25                  30

Leu Lys Met Glu Asn Leu Asn Leu Ile Lys Ala Pro Ile Pro Tyr Val
        35                  40                  45

Asp Ile His Asn Cys Asp Pro Ala Asn Pro Ser Glu Lys Asn Ser Leu
    50                  55                  60

Ser Ile Gln Tyr Cys Gly Ser Ile Arg Ser Val
65                  70                  75

<210> SEQ ID NO 12
<211> LENGTH: 53
<212> TYPE: PRT
<213> ORGANISM: Homo sapiens

<400> SEQUENCE: 12

Asp Ile Leu Asn Ile Lys Ile Ser His Phe Leu Lys Met Glu Ser Leu
1               5                   10                  15

Asn Phe Ile Arg Ala His Thr Pro Tyr Ile Asn Ile Tyr Asn Cys Glu
            20                  25                  30

Pro Ala Asn Pro Ser Glu Lys Asn Ser Pro Ser Thr Gln Tyr Cys Tyr
```

```
                    35                  40                  45

Ser Ile Gln Ser Leu
    50

<210> SEQ ID NO 13
<211> LENGTH: 53
<212> TYPE: PRT
<213> ORGANISM: Mus musculus

<400> SEQUENCE: 13

Asp Ile Leu Asn Met Thr Leu Ser His Phe Leu Lys Met Arg Arg Leu
1               5                   10                  15

Glu Leu Ile Gln Thr Ser Lys Pro Tyr Val Asp Ile Tyr Asp Cys Glu
            20                  25                  30

Pro Ser Asn Ser Ser Glu Lys Asn Ser Pro Ser Thr Gln Tyr Cys Asn
        35                  40                  45

Ser Ile Gln Ser Val
    50

<210> SEQ ID NO 14
<211> LENGTH: 54
<212> TYPE: PRT
<213> ORGANISM: Felis catus

<400> SEQUENCE: 14

Asp Ile Phe Asn Ile Ala Ile Ser His Phe Phe Lys Met Glu Asn Leu
1               5                   10                  15

Asn Leu Leu Lys Ser Pro Lys Pro Tyr Ile Asp Ile His Thr Cys Gln
            20                  25                  30

Pro Glu Ser Lys Pro Ser Glu Lys Asn Ser Leu Ser Ile Lys Tyr Cys
        35                  40                  45

Asp Ser Ile Arg Ser Val
    50
```

CANINE CD20 COMPOSITIONS

PRIORITY

This application claims the benefit of U.S. Application 60/575,172 filed May 28, 2004, which is incorporated herein by reference in its entirety.

BACKGROUND OF THE INVENTION

CD20 is a transmembrane protein that is expressed on more than 95% of B-lymphocytes. Expression at the cell surface occurs from the pre-B stage of development until differentiation to a plasma cell. The protein has several functions; it serves as a calcium channel, it is involved in intracellular signal transduction, and it can modulate cell growth and differentiation. In human medicine, anti-CD20 monoclonal antibody therapeutics (e.g.: RITUXAN® (Rituximab) by Genentech and IDEC Pharmaceuticals) have been successfully utilized to treat relapsed or refractory low-grade or follicular, CD20+, B-cell non-Hodgkin's lymphoma (NHL). RITUXAN® (Rituximab) has also been used in treating immune-mediated hemolytic anemia, immune-mediated thrombocytopenia, and systemic lupus erythematosus (SLE). RITUXAN® (Rituximab), however, does not bind canine B cells. See, Impellizeri et al., Vet. Cancer Society. 2003. Proceed. 23$^{rd}$ Ann. Conf., p. 2.

SUMMARY OF THE INVENTION

The invention provides canine CD20 nucleotide and protein sequences. These compositions are useful in the diagnosis and treatment of, e.g., CD20+ B-cell lymphoma, immune-mediated hemolytic anemia, immune-mediated thrombocytopenia, and systemic lupus erythematosus (SLE) in canines and felines.

One embodiment of the invention provides an isolated canine CD20 protein comprising SEQ ID NO:6.

Another embodiment of the invention provides a polypeptide comprising SEQ ID NO:6, wherein the polypeptide has one or more amino acid substitutions at about one to about 45 positions selected from amino acid positions 8, 9, 11, 12, 14, 15, 16, 17, 19, 21, 24, 25, 26, 27, 29, 30, 31, 32, 34, 35, 37, 43, 47, 51, 65, 73, 74, 75, 76, 77, 82, 83, 84, 94, 102, 105, 106, 108, 109, 112, 116, 118, 121, 131, 133, 134, 139, 141, 142, 143, 147, 150, 151, 153, 154, 155, 156, 157, 158, 159, 162, 163, 165, 166, 168, 170, 171, 172, 178, 180, 184, 187, 189, 192, 193, 194, 195, 196, 198, 199, 200, 201, 202, 205, 208, 218, 219, 221, 222, 223, 225, 226, 227, 228, 232, 234, 235, 240, 241, 242, 243, 244, 247, 248, 249, 251, 252, 253, 254, 259, 262, 270, 275, 277, 280, 282, 285, 288, 290, 292, 295, 296, and 297, wherein the polypeptide is not SEQ ID NO:7, SEQ ID NO:8, or SEQ ID NO:9 and wherein the polypeptide is isolated, purified and about 297 to about 300 amino acids long. The polypeptide can further comprise one or more amino acid sequences that are not canine amino acid sequences. The one or more amino acid substitutions can be conservative amino acid substitutions. The amino acid substitutions can be selected from the following substitutions:

| Amino Acid Position | Amino Acid Substitution |
| --- | --- |
| 8 | V |
| 9 | N |
| 11 | P |
| 12 | F |
| 14 | A |
| 15 | E |
| 16 | A |
| 17 | T |
| 19 | G |
| 21 | L, I |
| 24 | Q, N |
| 25 | S |
| 26 | G, A |
| 27 | P |
| 29 | P, V |
| 30 | L, N |
| 31 | F, L |
| 32 | R |
| 34 | T |
| 35 | S |
| 37 | L |
| 43 | S |
| 47 | K |
| 51 | A, P |
| 64 | M |
| 65 | T |
| 73 | P |
| 74 | A, M |
| 75 | G, E |
| 76 | I |
| 77 | F |
| 82 | L, V, M |
| 83 | S |
| 84 | V |
| 94 | Y |
| 102 | V |
| 105 | A |
| 106 | E |
| 108 | T |
| 109 | S |
| 112 | C |
| 116 | A |
| 118 | V |
| 121 | S |
| 131 | M |
| 133 | L |
| 134 | S |
| 139 | L |
| 141 | M |
| 142 | K, A |
| 143 | L |
| 147 | F |
| 150 | R |
| 151 | S, R |
| 153 | E |
| 154 | F |
| 155 | L |
| 156 | R, Q |
| 157 | T, S |
| 158 | H, S |
| 159 | T, K |
| 162 | I |
| 163 | N |
| 165 | Y |
| 166 | D, T |
| 168 | E, Q |
| 170 | S |
| 171 | K |
| 172 | S |
| 178 | P |
| 180 | T |
| 184 | Y, N, D |
| 187 | Q |
| 189 | L |
| 192 | S |
| 193 | I |
| 194 | L |
| 195 | S |
| 196 | A |

-continued

| Amino Acid Position | Amino Acid Substitution |
|---|---|
| 198 | L |
| 199 | V |
| 200 | S |
| 201 | A |
| 202 | L |
| 205 | E |
| 208 | I |
| 218 | R |
| 219 | T, M |
| 221 | T |
| 222 | R |
| 223 | S |
| 225 | A |
| 226 | N |
| 227 | DELETE |
| 228 | I |
| 232 | S |
| 234 | G |
| 235 | N |
| 240 | T, L |
| 241 | V |
| 242 | K |
| 243 | I, M |
| 244 | K |
| 247 | V, I, A |
| 248 | I |
| 249 | G |
| 251 | S |
| 252 | G |
| 253 | T, V |
| 254 | S |
| 259 | N |
| 262 | E |
| 270 | I |
| 275 | T, A |
| 277 | T, M |
| 280 | P |
| 282 | A |
| 285 | D |
| 288 | P |
| 290 | L |
| 292 | V |
| 295 | E |
| 296 | I |
| 297 | S, A |

The polypeptide comprises one or more of the following amino acid additions: an A after amino acid 104; an E after amino acid 169, and an E after amino acid 274.

Even another embodiment of the invention provides an isolated polypeptide comprising SEQ ID NO:10. The polypeptide can be present in a fusion protein.

Still another embodiment of the invention provides a polypeptide comprising SEQ ID NO: 10, wherein the polypeptide has about one to about 12 amino acid substitutions at positions 3, 5, 6, 7, 14, 15, 17, 18, 19, 20, 21, 22, 23, 26, 27, 29, 30, 32, 35, and 45, wherein the polypeptide is not SEQ ID NO:12, SEQ ID NO:13, or SEQ ID NO:14, and wherein the polypeptide is isolated, purified and is about 53 amino acids long. The amino acid substitutions can be conservative amino acid substitutions. The amino acid substitutions can be selected from the following substitutions:

| Amino Acid Position | Substitution |
|---|---|
| 3 | L |
| 5 | M |
| 6 | K, A |
| 7 | L |
| 11 | F |
| 14 | R |
| 15 | S, R |
| 17 | E |
| 18 | F |
| 19 | L |
| 20 | R, Q |
| 21 | T, S |
| 22 | H, S |
| 23 | T, K |
| 26 | I |
| 27 | N |
| 29 | Y |
| 30 | D, T |
| 32 | E, Q |
| 34 | S |
| 35 | K |
| 36 | S |
| 42 | P |
| 44 | T |
| 45 | K |
| 48 | N, Y, D |
| 51 | Q |
| 53 | L |

The polypeptide can comprise one or more amino acid sequences that are not canine amino acid sequences. The polypeptide can comprise an amino acid addition of E after amino acid number 33. The polypeptide can comprise SEQ ID NO:11.

Yet another embodiment of the invention provides an antibody or antigen binding portion thereof that specifically binds SEQ ID NO:6 or SEQ ID NO:10. The isolated antibody or antigen binding portion thereof can be a monoclonal antibody, a polyclonal antibody, or single chain antibody. The antibody can be produced by myeloma cell line ATCC PTA-6661 or ATCC PTA-6662. The antigen binding portion thereof can be a Fab fragment, a F(ab')$_2$ fragment, or a Fv fragment.

Another embodiment of the invention provides an isolated polynucleotide that encodes a canine CD20 protein. The polynucleotide can comprise SEQ ID NO:5. The isolated polynucleotide can comprise about 12 or more contiguous nucleic acids of SEQ ID NO:5.

Even another embodiment of the invention provides an isolated polynucleotide that encodes the extracellular domain of a canine CD20 protein.

Yet another embodiment of the invention provides a vector comprising a polynucleotide of the invention and a recombinant host cell that comprises a vector of the invention.

Still another embodiment of the invention provides a method of producing a recombinant cell that expresses a canine CD20 protein, or fragment thereof, comprising transfecting a cell with the vector of the invention. A canine CD20 polypeptide or a fragment thereof can be produced by expressing the polypeptide in the recombinant host cell of the invention.

Another embodiment of the invention provides a method of detecting a canine or feline CD20-positive B-lymphocyte. The method comprises contacting one or more antibodies that specifically bind to a polypeptide consisting of SEQ ID NO:6 or SEQ ID NO:10 with a test sample under conditions that allow B-lymphocyte/antibody complexes to form and detecting B-lymphocyte/antibody complexes. The detection of B-lymphocyte/antibody complexes is an indication that a canine or feline CD20-positive B-lymphocyte is present in the sample and the absence of B-lymphocyte/antibody complexes is an indication that a canine or feline CD20-positive B-lymphocyte is not present in the sample. The one or more antibodies can be monoclonal antibodies, polyclonal antibodies, or antibody fragments. The sample can be lymph node aspirate, serum, or whole blood.

Yet another embodiment of the invention provides a method of treating a canine or feline for CD20-positive B-cell lymphoma, immune-mediated hemolytic anemia, immune-mediated thrombocytopenia, or systemic lupus erythematosus (SLE) comprising administering an antibody of the invention to the canine or feline.

BRIEF DESCRIPTION OF THE DRAWINGS

FIG. 1 shows a portion of the nucleotide sequence for canine CD20 from canine peripheral blood mononuclear cell cDNA (SEQ ID NO:1).

FIG. 2 shows the translated polypeptide (SEQ ID NO:4) of SEQ ID NO:1 aligned with comparable regions of human CD 20 (SEQ ID NO:2) and mouse CD20 (SEQ ID NO:3).

FIG. 3 shows the full-length polynucleotide of canine CD20 (SEQ ID NO:5)

FIG. 4 shows the full-length polypeptide sequence (SEQ ID NO:6) for canine CD20 The amino acid sequence was deduced from cDNA sequence analysis.

FIG. 5 shows the alignment of the full length canine CD20 polypeptide (SEQ ID NO:6) with that of human (SEQ ID NO:7), mouse (SEQ ID NO:8) and cat (SEQ ID NO:9). The canine sequence is most similar to the feline sequence (84% identical) and less similar to that of human (74% identical) and mouse (68% identical).

FIG. 8 shows a 53-mer polypeptide of the predominant extracellular domain of canine CD20 (SEQ ID NO:10) that was synthesized alone and in conjunction with a murine T-cell epitope from ovalbumin (SEQ ID NO:11).

FIG. 13 shows the scatter plots obtained using the colloidal gold labeled F7A5 monoclonal antibody on a lymph node aspirate from a normal dog as analyzed by a point of care hematology instrument. Panel A depicts the unlabeled control and F7A5 labeled cells for gating on small lymphocytes, while panel B depicts the same comparison when gating on medium lymphocytes.

DETAILED DESCRIPTION OF THE INVENTION

Polypeptides

Figure 6:
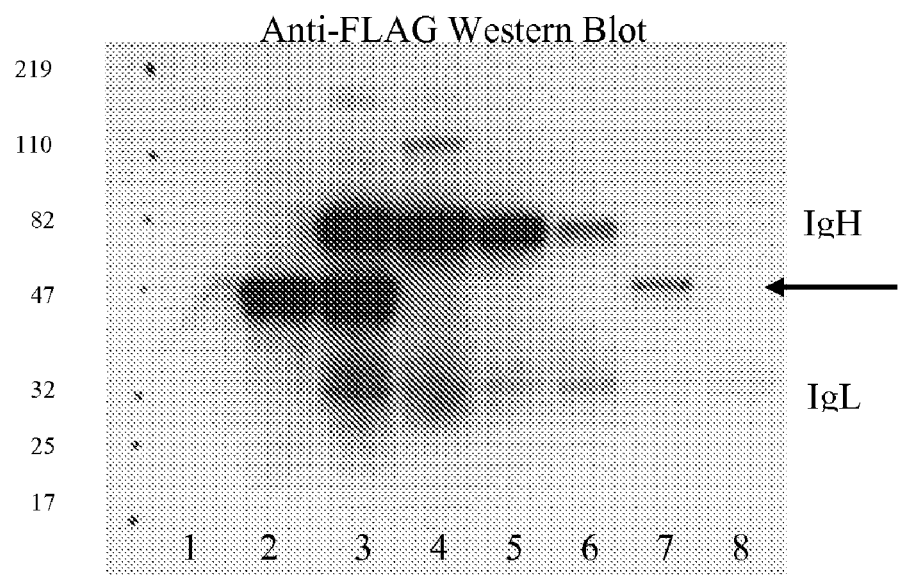
FIG. 6 is an anti-FLAG Western blot demonstrating expression of canine CD20 in COS7 cells. Lane I is an empty plasmid control, lane 2 is total cell lysate of cells transiently transfected with canine CD20, lanes 3-8 are total cell lysates from transfected cells immunoprecipitated with either anti-FLAG (3), anti-CD20 monoclonals (4,5), or anti-CD20 polyclonal antibodies (6-8).

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Polypeptides of the invention comprise full-length canine CD20 and fragments thereof. One embodiment of the invention provides an isolated polypeptide comprising SEQ ID NO:6 or SEQ ID NO:10. Another embodiment of the invention provides a polypeptide comprising SEQ ID NO:10 and having amino acid substitutions, for example, conservative amino acid substitutions, at one or more positions (for example, about 1, 2, 3, 4, 5, 6, 7, 8, 9, 10, 11, 12, 13, 14, 15, 20, 24 or more amino acid substitutions) selected from amino acid positions 3, 5, 6, 7, 14, 15, 17, 18, 19, 20, 21, 22, 23, 26, 27, 29, 30, 32, 35, and 45 of SEQ ID NO:10, wherein the polypeptide is not SEQ ID NO:12 or SEQ ID NO:13, or SEQ ID NO:14 and wherein the polypeptide is isolated, purified and is about 53 amino acids long. An amino acid addition of "E" can occur after amino acid number 33. In one embodiment of the invention SEQ ID NO:10 has one or more substituted amino acids (for example, 1, 2, 3, 4, 5, 6, 7, 8, 9, 10, 11, 12, 13, 14, 15, 20, or 24 amino acid substitutions) as shown in Table 1 and the polypeptide is not SEQ ID NO:12, SEQ ID NO:13, or SEQ ID NO:14 and the polypeptide is isolated, purified and about 53 amino acids long.

TABLE 1

| Amino Acid Position | Substitution |
|---|---|
| 3 | L |
| 5 | M |
| 6 | K, A |
| 7 | L |
| 11 | F |
| 14 | R |
| 15 | S, R |
| 17 | E |
| 18 | F |
| 19 | L |
| 20 | R, Q |
| 21 | T, S |
| 22 | H, S |

TABLE 1-continued

| Amino Acid Position | Substitution |
|---|---|
| 23 | T, K |
| 26 | I |
| 27 | N |
| 29 | Y |
| 30 | D, T |
| 32 | E, Q |
| 34 | S |
| 35 | K |
| 36 | S |
| 42 | P |
| 44 | T |
| 45 | K |
| 48 | N, Y, D |
| 51 | Q |
| 53 | L |

Another embodiment of the invention provides a polypeptide comprising SEQ ID NO:6 having amino acid substitutions, for example, conservative amino acid substitutions, at one or more positions (e.g., about 1, 2, 3, 4, 5, 10, 15, 20, 25, 30, 35, 40, 45, 50, 55, 60 or more amino acid substitutions) selected from amino acid positions 8, 9, 11, 12, 14, 15, 16, 17, 19, 21, 24, 25, 26, 27, 29, 30, 31, 32, 34, 35, 37, 43, 47, 51, 65, 73, 74, 75, 76, 77, 82, 83, 84, 94, 102, 105, 106, 108, 109, 112, 116, 118, 121, 131, 133, 134, 139, 141, 142, 143, 147, 150, 151, 153, 154, 155, 156, 157, 158, 159, 162, 163, 165, 166, 168, 170, 171, 172, 178, 180, 184, 187, 189, 192, 193, 194, 195, 196, 198, 199, 200, 201, 202, 205, 208, 218, 219, 221, 222, 223, 225, 226, 227, 228, 232, 234, 235, 240, 241, 242, 243, 244, 247, 248, 249, 251, 252, 253, 254, 259, 262, 270, 275, 277, 280, 282, 285, 288, 290, 292, 295, 296, 297 wherein the polypeptide is not SEQ ID NO:7, SEQ ID NO:8, or SEQ ID NO:9 and wherein the polypeptide is isolated, purified, and about 297 to about 299 amino acids long. In one embodiment of the invention SEQ ID NO:6 has one or more (e.g., 1, 2, 3, 4, 5, 10, 15, 20, 25, 30, 35, 40, 45, 50, 55, 60 or more) substituted amino acids as shown in Table 2 and the polypeptide is not SEQ ID NO:7, SEQ ID NO:8, or SEQ ID NO:9 and the polypeptide is isolated, purified and about 297 to about 300 amino acids long. Additionally, amino acid additions can occur as follows: an A after amino acid 104; an E after amino acid 169, an E after amino acid 274 of SEQ ID NO:6.

TABLE 2

| Amino Acid Position | Amino Acid Substitution |
|---|---|
| 8 | V |
| 9 | N |
| 11 | P |
| 12 | F |
| 14 | A |
| 15 | E |
| 16 | A |
| 17 | T |
| 19 | G |
| 21 | L, I |
| 24 | Q, N |
| 25 | S |
| 26 | G, A |
| 27 | P |
| 29 | P, V |
| 30 | L, N |
| 31 | F, L |
| 32 | R |
| 34 | T |

TABLE 2-continued

| Amino Acid Position | Amino Acid Substitution |
|---|---|
| 35 | S |
| 37 | L |
| 43 | S |
| 47 | K |
| 51 | A, P |
| 64 | M |
| 65 | T |
| 73 | P |
| 74 | A, M |
| 75 | G, E |
| 76 | I |
| 77 | F |
| 82 | L, V, M |
| 83 | S |
| 84 | V |
| 94 | Y |
| 102 | V |
| 105 | A |
| 106 | E |
| 108 | T |
| 109 | S |
| 112 | C |
| 116 | A |
| 118 | V |
| 121 | S |
| 131 | M |
| 133 | L |
| 134 | S |
| 139 | L |
| 141 | M |
| 142 | K, A |
| 143 | L |
| 147 | F |
| 150 | R |
| 151 | S, R |
| 153 | E |
| 154 | F |
| 155 | L |
| 156 | R, Q |
| 157 | T, S |
| 158 | H, S |
| 159 | T, K |
| 162 | I |
| 163 | N |
| 165 | Y |
| 166 | D, T |
| 168 | E, Q |
| 170 | S |
| 171 | K |
| 172 | S |
| 178 | P |
| 180 | T |
| 184 | Y, N, D |
| 187 | Q |
| 189 | L |
| 192 | S |
| 193 | I |
| 194 | L |
| 195 | S |
| 196 | A |
| 198 | L |
| 199 | V |
| 200 | S |
| 201 | A |
| 202 | L |
| 205 | E |
| 208 | I |
| 218 | R |
| 219 | T, M |
| 221 | T |
| 222 | R |
| 223 | S |
| 225 | A |
| 226 | N |
| 227 | DELETE |

TABLE 2-continued

| Amino Acid Position | Amino Acid Substitution |
|---|---|
| 228 | I |
| 232 | S |
| 234 | G |
| 235 | N |
| 240 | T, L |
| 241 | V |
| 242 | K |
| 243 | I, M |
| 244 | K |
| 247 | V, I, A |
| 248 | I |
| 249 | G |
| 251 | S |
| 252 | G |
| 253 | T, V |
| 254 | S |
| 259 | N |
| 262 | E |
| 270 | I |
| 275 | T, A |
| 277 | T, M |
| 280 | P |
| 282 | A |
| 285 | D |
| 288 | P |
| 290 | L |
| 292 | V |
| 295 | E |
| 296 | I |
| 297 | S, A |

The basic and novel characteristics of polypeptides of the invention that consist essentially of SEQ ID NO:6 or SEQ ID NO:10 are that they consist essentially of the sequences shown in SEQ ID NO:6 and SEQ ID NO:10 and that they specifically bind to an antibody, antibody fragment, or single-chain antibody of the invention.

One of skill in the art would expect that amino acid substations and/or additions could be made in the amino acid sequences of SEQ ID NO:6 or SEQ ID NO:10 as described above, wherein the amino acid sequences would retain their functional activity. For example, a F7A5 monoclonal antibody (see Example 6), which is specific for SEQ ID NO:10 specifically binds both feline and canine CD20-positive B lymphocytes (see Example 7 and 8), despite the fact that sequences of feline and canine CD20 are not 100% homologous.

An isolated polypeptide is a molecule of amino acids that is not immediately contiguous with one or both canine flanking amino acid sequences that the molecule is normally associated with in nature. An isolated polypeptide is also a molecule of amino acids that forms part of a hybrid polypeptide comprising additional non-canine polypeptide sequences that can be, for example, a fusion protein.

The invention also includes functionally active variants of SEQ ID NO:6 and SEQ ID NO:10. Functionally active variants of SEQ ID NO:6 or SEQ ID NO:10 can comprise one or more of the amino acid substitutions as described above. In one embodiment, a functionally active variant polypeptide includes an amino acid sequence at least about 60% identical to a sequence shown as SEQ ID NO:6 and SEQ ID NO:10. Preferably, the polypeptide is at least 55%, 60%, 65%, 70%, 75%, 80%, 85%, 90%, 95%, 98%, 99% or more identical to SEQ ID NO:6 or SEQ ID NO:10 and specifically binds to an antibody of the invention. Functionally active variant polypeptides and polypeptides of the invention also specifically bind to an antibody, such as a monoclonal antibody, that is raised to a polypeptide shown in SEQ ID NO:6 or SEQ ID NO:10.

Polypeptides of the invention specifically bind to an antibody of the invention. In this context "specifically binds" means that the polypeptide recognizes and binds to an antibody of the invention with greater affinity than to other, non-specific molecules. For example, an antibody raised against an antigen (polypeptide) to which it binds more efficiently than to a non-specific protein can be described as specifically binding to the antigen. Binding specifically can be tested using, for example, an enzyme-linked immunosorbant assay (ELISA), a radioimmunoassay (RIA), or a western blot assay using methodology well known in the art.

A polypeptide is a functionally active variant if it reacts substantially the same as a polypeptide shown in SEQ ID NO:6 or SEQ ID NO:10 in an assay such as an immunohistochemical assay, an ELISA, an RIA, or a western blot assay, e.g. has 90-110% of the specific binding activity of the original polypeptide. In one embodiment, the assay is a competition assay wherein the functionally active variant polypeptide is capable of reducing binding of a polypeptide shown in SEQ ID NO:6 or SEQ ID NO:10 to a corresponding antibody, antibody fragment, or single-chain antibody by about 80, 95, 99, or 100%.

Functionally active variants can also comprise "polypeptide fragments" of the invention. Polypeptide fragments comprise or consist essentially of about 15, 20, 30, 40, 50, 100, 150, 200, or 299 amino acids of SEQ ID NO:6 or SEQ ID NO:10.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means amino acid sequence (or nucleic acid sequence) similarity and has an art recognized meaning. Sequences with identity share identical or similar amino acids (or nucleic acids). Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

Functionally active variants of SEQ ID NO:6 or SEQ ID NO:10 retain substantially the same functional activity of the original polypeptide or fragment. Naturally occurring functionally active variants such as allelic variants and species variants and non-naturally occurring functionally active variants are included in the invention and can be produced by, for example, mutagenesis techniques or by direct synthesis.

A functionally active variant differs by about, for example, 1, 2, 3, 4, 5, 10, 20, 30, 40, 50, 60 or more amino acid residues from a polypeptide shown in SEQ ID NO:6 or SEQ ID NO:10 or a fragment thereof. Where this comparison requires alignment the sequences are aligned for maximum homology. The site of variation can occur anywhere in the polypeptide, as long as activity substantially similar to a polypeptide shown in SEQ ID NO:6 and SEQ ID NO:10 is maintained.

Guidance concerning how to make phenotypically silent amino acid substitutions is provided in Bowie et al., *Science*, 247:1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. See e.g., FIG. 5. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific binding activity of the polypeptide.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., *Science*, 244:1081-1085 (1989)). The resulting variant molecules can then be tested for specific binding to antibodies of the invention.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a polypeptide functionally active variant to a polypeptide by replacing an amino acid that does not influence the function of a polypeptide can be accomplished by one skilled in the art.

In one embodiment of the invention, a polypeptide of the invention is derived from a canine. A polypeptide of the invention can be isolated from cells or tissue sources using standard protein purification techniques. Polypeptides of the invention can also be synthesized chemically or produced by recombinant DNA techniques. For example, a polypeptide of the invention can be synthesized using conventional peptide synthesizers. Additionally, a polynucleotide encoding a polypeptide of the invention can be introduced into an expression vector that can be expressed in a suitable expression system using techniques well known in the art. A variety of bacterial, yeast, plant, mammalian, and insect expression systems are available in the art and any such expression system can be used. Optionally, a polynucleotide encoding a polypeptide of the invention can be translated in a cell-free translation system.

A functionally active variant polypeptide can also be isolated using a hybridization technique. Briefly, DNA having a high homology to the whole or part of a nucleic acid sequence encoding SEQ ID NO:6 or SEQ ID NO:10 is used to prepare a functionally active polypeptide. Therefore, a polypeptide of the invention also includes polypeptides that are functionally equivalent to a SEQ ID NO:6 or SEQ ID NO:10 polypeptide and are encoded by a nucleic acid molecule that hybridizes with a nucleic acid encoding SEQ ID NO:6 or SEQ ID NO:10 or a complement thereof. One of skill in the art can easily determine nucleic acid sequences that encode polypeptides of the invention using readily available codon tables. As such, these nucleic acid sequences are not presented herein.

The stringency of hybridization for a nucleic acid encoding a polypeptide that is a functionally active variant is, for example, 10% formamide, 5×SSPE, 1× Denhart's solution, and 1× salmon sperm DNA (low stringency conditions). More preferable conditions are, 25% formamide, 5×SSPE, 1× Denhart's solution, and 1× salmon sperm DNA (moderate stringency conditions), and even more preferable conditions are, 50% formamide, 5×SSPE, 1× Denhart's solution, and 1× salmon sperm DNA (high stringency conditions). However, several factors influence the stringency of hybridization other than the above-described formamide concentration, and one skilled in the art can suitably select these factors to accomplish a similar stringency.

Nucleic acid molecules encoding a functionally active variant polypeptide can also be isolated by a gene amplification method such as PCR using a portion of a nucleic acid molecule DNA encoding a polypeptide shown in SEQ ID NO:6 or SEQ ID NO:10 as the probe.

Polypeptides of the invention can also comprise those that arise as a result of the existence of multiple genes, alternative transcription events, alternative RNA splicing events, and alternative translational and postranslational events. A polypeptide can be expressed in systems, e.g., cultured cells, which result in substantially the same postranslational modifications present as when the polypeptide is expressed in a native cell, or in systems that result in the alteration or omission of postranslational modifications, e.g., glycosylation or cleavage, present when expressed in a native cell.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. A fusion protein is two or more different amino acid sequences operably linked to each other. A fusion protein construct can be synthesized chemically using organic compound synthesis techniques by joining individual polypeptide fragments together in fixed sequence. A fusion protein construct can also be expressed by a genetically modified host cell (such as E. coli) cultured in vitro, which carries an introduced expression vector bearing specified recombinant DNA sequences encoding the amino acids residues in proper sequence. The heterologous polypeptide can be fused, for example, to the N-terminus or C-terminus of a polypeptide of the invention. A polypeptide of the invention can also comprise homologous amino acid sequences, i.e., other CD20 or CD20-derived sequences. More than one polypeptide of the invention can be present in a fusion protein. Fragments of polypeptides of the invention can be present in a fusion protein of the invention. A fusion protein of the invention can comprise, e.g., one or more of SEQ ID NO:6, SEQ ID NO:10, fragments thereof, or combinations thereof.

Polypeptides of the invention can be in a multimeric form. That is, a polypeptide can comprise one or more copies of SEQ ID NO:6, SEQ ID NO:10 or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody reactive against canine CD20. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay a canine CD20 polypeptide, such as a 100mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from cells.

An immunogenic polypeptide of the invention can comprise an amino acid sequence shown in, e.g., SEQ ID NO:6 or SEQ ID NO:10. An immunogenic polypeptide can elicit antibodies or other immune responses (e.g., T-cell responses of the immune system) that recognize epitopes of polypeptides having SEQ ID NO:6 or SEQ ID NO:10. An immunogenic polypeptide of the invention can also be a fragment of a polypeptide that has an amino acid sequence shown in SEQ ID NO:6 or SEQ ID NO:10. An immunogenic polypeptide fragment of the invention can be about 5, 6, 7, 8, 9, 10, 11, 12, 13, 14, 15, 16, 17, 18, 19, or 20 amino acids in length.

Polynucleotides

Polynucleotides of the invention contain less than an entire canine genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% pure by dry weight. Purity can be measured by a method such as column chromatography, polyacrylamide gel electrophoresis, or HPLC analysis. The polynucleotides of the invention encode the polypeptides described above. In one embodiment of the invention the polynucleotides encode polypeptides shown in, e.g., SEQ ID NO:6 or SEQ ID NO:10 or combinations thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

The polynucleotides of the invention encode the polypeptides described above, as well as fragments thereof. A fragment can be about 10, 12, 15, 20, 50, 75, 100, 125, 250, 300, 400, 500, 600, 700, 800, 900, 1,000 or more polynucleotides. One of skill in the art can obtain the polynucleotide sequence of the invention using the disclosed polypeptide sequence and codon tables. Polynucleotides can contain naturally occurring polynucleotides or sequences that differ from those of any naturally occurring sequences or polynucleotides. In one embodiment of the invention, a polynucleotide of the invention is derived from a mammal, such as a dog. Polynucleotides of the invention can differ from naturally occurring nucleic acids, but still encode naturally occurring amino acids due to the degeneracy of the genetic code. Polynucleotides of the invention can also comprise other heterologous nucleotide sequences, such as sequences coding for linkers, signal sequences, amino acid spacers, heterologous signal sequences, TMR stop transfer sequences, transmembrane domains, or ligands useful in protein purification such as glutathione-S-transferase, histidine tag, and staphylococcal protein A. Polynucleotides of the invention can also comprise other homologous nucleotide sequences, i.e., other CD20 or CD20-derived sequences.

An isolated polynucleotide is a nucleic acid molecule that is not immediately contiguous with one or both of the 5' and 3' flanking sequences with which it is normally contiguous when present in a naturally occurring genome. Therefore, an isolated polynucleotide can be, for example, a polynucleotide that is incorporated into a vector, such as a plasmid or viral vector, a polynucleotide that is incorporated into the genome of a heterologous cell (or the genome of a homologous cell, but at a site different from that where it naturally occurs); and a polynucleotide that exists as a separate molecule such as a polynucleotide produced by PCR amplification, chemically synthesis, restriction enzyme digestion, or in vitro transcription. An isolated polynucleotide is also a nucleic acid molecule, such as a recombinant nucleic acid molecule that forms part of hybrid polynucleotide encoding additional polypeptide sequences that can be used for example, in the production of a fusion protein.

A polynucleotide can also comprise one or more expression control sequences such as promoters or enhancers, for example. A polynucleotide of the invention can be present in a vector, such as, for example, an expression vector. If desired, polynucleotides can be cloned into an expression vector comprising, for example, promoters, enhancers, or other expression control sequences that drive expression of the polynucleotides of the invention in host cells. The polynucleotides can be operably linked to the expression control sequences. An expression vector can be, for example, a plasmid, such as pBR322, pUC, or ColE1, or an adenovirus vector, such as an adenovirus Type 2 vector or Type 5 vector. Vectors suitable for use in the present invention include, for example, bacterial vectors, mammalian vectors, viral vectors (such as retroviral, adenoviral, adeno-associated viral, herpes virus, simian virus 40 (SV40), and bovine papilloma virus vectors) and baculovirus-derived vectors for use in insect cells. Polynucleotides in such vectors are preferably operably linked to a promoter, which is selected based on, e.g., the cell type in which expression is sought.

Host cells into which vectors, such as expression vectors, comprising polynucleotides of the invention can be introduced include, for example, prokaryotic cells (e.g., bacterial cells) and eukaryotic cells (e.g., yeast cells; insect cells; and mammalian cells). Such host cells are available from a number of different sources that are known to those skilled in the art, e.g., the American Type Culture Collection (ATCC), Rockville, Md. Host cells into which the polynucleotides of the invention have been introduced, as well as their progeny, even if not identical to the parental cells, due to mutations, are included in the invention.

Methods for introducing polynucleotides of the invention (e.g., vectors comprising the polynucleotides or naked polynucleotides) into cells, either transiently or stably, are well known in the art. For example, transformation methods using standard $CaCl_2$, $MgCl_2$, or RbCl methods, protoplast fusion methods or transfection of naked or encapsulated nucleic acids using calcium phosphate precipitation, microinjection, viral infection, and electroporation.

One embodiment of the invention provides methods of producing a recombinant cell that expresses a canine CD20 protein, or fragment thereof, comprising transfecting a cell with a vector comprising the polynucleotide of the invention. A canine CD20 protein, or fragment thereof, can then be produced by expressing the polypeptide in the recombinant host cell.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

Polynucleotides can be synthesized in the laboratory, for example, using an automatic synthesizer. An amplification method such as PCR can be used to amplify polynucleotides from either genomic DNA or cDNA encoding the polypeptides.

Polynucleotides and fragments thereof of the invention can be used, for example, as probes or primers to detect the presence of canine CD20 polynucleotides in a, such as a biological sample. A biological sample can be, e.g., lymph node or tissue aspirate, serum, whole blood, cellular suspension, or fluid effusion. The ability of such probes to specifically hybridize to polynucleotide sequences will enable them to be of use in detecting the presence of complementary sequences in a given sample. Polynucleotide probes of the invention can hybridize to complementary sequences in a sample such as a biological sample, for example, lymph tissue, thereby detecting the presence or absence of canine CD20 polynucleotides in samples. Polynucleotides from the sample can be, for example, subjected to gel electrophoresis or other size separation techniques or can be dot blotted without size separation. The polynucleotide probes are preferably labeled. Suitable labels, and methods for labeling probes are known in the art, and include, for example, radioactive labels incorporated by nick translation or by kinase, biotin, fluorescent probes, and chemiluminescent probes. The polynucleotides from the sample are then treated with the probe under hybridization conditions of suitable stringencies.

Depending on the application, varying conditions of hybridization can be used to achieve varying degrees of selectivity of the probe towards the target sequence. For applications requiring high selectivity, relatively stringent conditions can be used, such as low salt and/or high temperature conditions, such as provided by a salt concentration of from about 0.02 M to about 0.15 M at temperatures of from about 50° C. to about 70° C. For applications requiring less selectivity, less stringent hybridization conditions can be used. For example, salt conditions from about 0.14 M to about 0.9 M salt, at temperatures ranging from about 20° C. to about 55° C. The presence of a hybridized complex comprising the probe and a complementary polynucleotide from the sample indicates the presence of the microbe or polynucleotide sequence in the sample.

Antibodies and Antibody Fragments

Antibodies, such as monoclonal and polyclonal antibodies, that specifically bind polypeptides of the invention are part of the invention. These antibodies can be made by using a polypeptide or a polypeptide fragment that contains an epitope present in a polypeptide shown in SEQ ID NO:6, SEQ ID NO:10 or SEQ ID NO:11 as an immunogen in standard antibody production methods (see e.g., Kohler et al., Nature, 256:495, 1975; Ausubel et al. (1992) Current Protocols in Molecular Biology, John Wylie and Sons, Inc. New York, N.Y.; Harlow and Lane, Eds, (1988) Current Edition, Antibodies: A Laboratory Manual, Cold Spring Harbor Press, N.Y). Antibodies can also be made using DNA immunization techniques using nucleic acid sequence coding for polypeptides SEQ ID NO:6, SEQ ID NO:10, SEQ ID NO:11 or fragments thereof in, e.g., standard mammalian expression vectors. See e.g., Chambers et al., 2003 Nature Biotechnology 21: 1088-1092; Tang et al. Nature. 1992 Mar. 12; 356 (6365):152-4; Barry et al., Biotechniques. 1994 April; 16(4): 616-8, 620.

An antibody is an intact immunoglobulin molecule, a fragment of an immunoglobulin molecule, such as Fab, Fab', $F(ab')_2$, $F(ab)_2$, Fv, sFv, or a single-chain antibody or fragments thereof, that specifically binds to a polypeptide of the invention (e.g., SEQ ID NO:6 or SEQ ID NO:10 and fragments thereof). Antibody fragments retain some ability to selectively bind to the antigen (e.g., a polypeptide of the invention) from which they are derived, and can be made using well known methods in the art. In one embodiment of the invention, an antibody, antibody fragment or single-chain antibody comprises all such antibodies that specifically bind to a polypeptide of the invention (e.g., SEQ ID NO:6 or SEQ ID NO:10 and fragments thereof).

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that the polypeptide recognizes and binds to an antibody of the invention with greater affinity than to other, non-specific molecules. For example, an antibody raised against an antigen (e.g., a polypeptide) to which it binds more efficiently than to a non-specific protein can be described as specifically binding to the antigen. Binding specifically can be tested using, for example, an enzyme-linked immunosorbant assay (ELISA), a radioimmunoassay (RIA), or a western blot assay using methodology well known in the art.

Antibodies of the invention can be present in an antibody fusion protein. An antibody fusion protein refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

Polypeptides of the invention comprise at least one epitope. An epitope is an antigenic determinant of a polypeptide. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span the entire polypeptide sequence, can be prepared by proteolytic cleavage. By starting with, for example, 100-mer polypeptide fragments, each fragment can be tested for the presence of epitopes recognized in, for example, an enzyme-linked immunosorbent assay (ELISA). In an ELISA assay a polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific adsorbtion is blocked, and any unbound antibody and other proteins are washed away. Antibody binding is detected by, for example, a reaction that converts a colorless indicator reagent into a colored reaction product. Progressively smaller and overlapping fragments can then be tested from an identified 100-mer to map the epitope of interest.

Antigens that can be used in producing antibodies of the invention include polypeptides and polypeptide fragments of the invention. A polypeptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize an animal (e.g., a mouse, a rat, or a rabbit). In addition to such carriers, well known adjuvants can be administered with the antigen to facilitate induction of a strong immune response.

Polyclonal and monoclonal antibodies can be purified, for example, by binding to, and elution from, a matrix containing a polypeptide or polypeptide fragment of the invention to which the antibodies were raised. Additional methods for antibody purification and concentration are well known in the art and can be practiced with the antibodies of the invention. Anti-idiotype antibodies corresponding to polypeptides of the invention are also included in the invention, and can be produced using standard methods.

An antibody and antigen (e.g., a polypeptide or polypeptide fragment of the invention) specifically bind to each other if they bind to each other with greater affinity than to other, non-specific molecules. For example, an antibody raised against an antigen to which it binds more efficiently than to a non-specific protein can be described as specifically binding to the antigen.

In one embodiment of the invention an antibody of the invention specifically binds canine CD20. Antibodies of the invention can be used, for example, to detect canine CD20 polypeptides in a biological sample. Antibodies of the invention can be used in vitro or in vivo for immunodiagnosis. The antibodies are suited for use in, for example, immunoassays in which they are in liquid phase or bound to a solid phase carrier (e.g., a glass, polystyrene, polypropylene, polyethylene, dextran, nylon, amylase, natural and modified cellulose, polyacrylamide, agarose, or magnetite carrier). The antibodies used in such immunoassays can be detectably labeled (e.g., with an enzyme, a radioisotope, a fluorescent compound, a colloidal metal, a chemiluminescent compound, a phosphorescent compound, or a bioluminescent compound) using any of several standard methods that are well known in the art. Examples of immunoassays in which the antibodies of the invention can be used include, e.g., competitive and non-competitive immunoassays, which are carried out using either direct or indirect formats. Examples of such immunoassays include radioimmunoassays (RIA), flow cytometry, and sandwich assays (e.g., enzyme-linked immunosorbent assays (ELISAs)). RT-PCR assays can also be used to quantitatively detect canine CD20. Detection of antigens using the antibodies of the invention can be done using immunoassays that are run in either forward, reverse, or simultaneous modes, including immunohistochemical assays on physiological samples. Other immunoassay formats are well known in the art, and can be used in the invention.

Antibodies of the invention can be chimeric antibodies, for example, humanized or caninized antibodies. A humanized antibody, like a mouse-human chimeric antibody, can be prepared, for example, as follows: (1) isolate the gene encoding the antibody of the present invention from antibody-producing mouse cells; (2) replace the constant region of the H chain of the antibody with that of the human IgE; and (3) introduce into, for example, mouse myeloma J558L cells (See, Neuberger et al., Nature 314:268-270 (1985)). Alternatively, human antibodies or canine antibodies, for example, can be prepared by immunizing mice whose immune systems have been replaced with that of humans or canines with a polypeptide or polypeptide fragment of the present invention.

Antibodies that specifically bind canine CD20 antigens (e.g., CD20 polypeptides), are particularly useful for detecting the presence of CD20 antigens in a sample, such as a lymph node or tissue aspirate, serum, whole blood, cellular suspension, or fluid effusion sample from a canine or feline. An immunoassay for CD20 antigen can utilize one antibody or several antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of a CD20 antigen. Supports include, for example, glass, polystyrene, polypropylene, polyethylene, dextran, nylon, amylases, natural and modified celluloses, polyacrylamides, agaroses and magletite.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease. By measuring the increase or decrease of CD20-positive cells in a test sample from an animal, it can be determined whether a particular therapeutic regiment aimed at ameliorating the disorder is effective.

Methods of Treatment

Antibodies of the invention can used to treat canine CD20+ B-cell lymphoma, immune-mediated hemolytic anemia, immune-mediated thrombocytopenia, and systemic lupus erythematosus (SLE).

The invention also encompasses multimodal therapeutic methods wherein anti-CD20 antibody administration is supplemented with chemotherapy, or by administration of therapeutic proteins, such as immunoconjugates and antibody fusion proteins.

In general, the dosage of administered anti-CD20 antibodies, anti-CD20 antibody components, immunoconjugates, and fusion proteins will vary depending upon such factors as the canine's age, weight, sex, general medical condition and previous medical history. Typically, it is desirable to provide the recipient with a dosage of antibody component, immunoconjugate or fusion protein which is in the range of from about 1 pg/kg to 10 mg/kg (amount of agent/body weight of canine), although a lower or higher dosage also may be administered as circumstances dictate.

Administration of antibody components, immunoconjugates or fusion proteins to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration can be by continuous infusion or by single or multiple boluses.

Compositions of the invention can comprise anti-CD20 antibodies and a pharmaceutically acceptable buffer, for example, sterile saline, sterile buffered water, propylene glycol. Methods for preparing administrable agents, such as parenterally administrable agents, are described in Pharmaceutical Carriers & Formulations, Martin, Remington's Pharmaceutical Sciences, 15th Ed. (Mack Pub. Co., Easton, Pa. 1975), which is incorporated herein by reference.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Cloning Canine CD20:

The nucleotide sequence for canine CD20 has not been published or deposited in NCBI/GenBank. Using primers deposited in GenBank from an unpublished study using sequence tagged sites in the canine genome (Accession: L77424, L77425), a portion of the gene sequence for canine CD20 was amplified from canine peripheral blood mononuclear cell (PBMC) cDNA (SEQ ID NO: 1 FIG.). Specifically, PBMCs were purified from 8m1 of canine whole blood using Ficoll-Paque PLUS according to the manufacturer's instructions (Amersham Biosciences). The PBMCs were resuspended in Trizol (Invitrogen) and RNA was harvested as described in the product insert. Using 2.5 µg of this RNA and THERMOSCRIPT™ RT (reverse transcriptase) (Invitrogen), canine PBMC cDNA was generated using oligo-dT primers according to the product insert.

From this gene sequence, primers were designed for use with 5' and 3' RACE (Rapid Amplification of cDNA Ends) using a commercially available kit (SMART™ RACE, BD Biosciences-Clontech). The 5'RACE was successful using the kit according to the manufacturer's instructions. However, the 3' RACE product was incomplete, likely due to secondary structure in the mRNA. The complete elucidation of the 3' sequence required the use of a more temperature stable reverse transcriptase THERMOSCRIPT™ RT (reverse transcriptase), Invitrogen). The 3' RACE cDNA was synthesized from 2.5 µg of canine RNA with 1 µl of THERMO- SCRIPT™ RT (reverse transcriptase) at 60°C. for 15 minutes, followed by incubation at 65° C. for 30 minutes. This modification to the existing RACE technique resulted in a complete 3' sequence for canine CD20. The full length nucleotide and translated polypeptide sequences are shown in FIGS. 3 and 4 (SEQ ID NO: 5 and 6), respectively. An alignment of the full-length sequences for human, mouse, feline and canine CD20 is shown in FIG. 5. Canine CD20 is only 74% identical to human CD20 and 68% identical to murine CD20.

Example 2

Expression of Canine CD20:

The full-length nucleic acid sequence for canine CD20 was amplified from canine cDNA using a proof-reading Taq (High Fidelity Taq, Roche) and subcloned into a commercially available expression vector (pCMV4AFLAG; Stratagene) at the NotI/EcoRI sites using standard molecular biology procedures. The expression plasmid was transformed into E.coli and purified using a Maxi-Prep kit from Qiagen. The purified plasmid was transiently transfected into COS7 cells (ATCC CRL-1651) using either Lipofectamine (Invitrogen) or FUGENE® 6 (transfection reagent) (Roche) according to the manufacturer's instructions. Two days post-transfection, the cells were washed twice with phosphate buffered saline (PBS, pH 7.2), scraped from the surface of the well in buffer, and pelleted by centrifugation. The resulting cell pellet was lysed in a Triton X-100 lysis buffer (50 mM Tris (pH 7.5), 150 mM NaCl, 0.5% Triton X-100, 2 mM EDTA, Protease Inhibitor V (CalBiochem)) for 30 minutes on ice followed by centrifugation of cell debris at 4° C. for 15 minutes. For total cell lysate, the resulting supernatant was boiled in an equal volume of SDS sample buffer and loaded onto 4-20% SDS-PAGE gels (Pierce). For immunoprecipitation, the lysate was incubated with either 5 μl of anti-FLAG M2 monoclonal antibody, 2.5 μl of monoclonal anti-CD20 antibody (Biogenex MU265-UC and MU238-UC), or 5 μl of polyclonal anti-CD20 (Santa Cruz Biotechnology sc-15361, sc-7736, or LabVision RB-9013) overnight at 4° C. with mixing. A 1:1 slurry of Protein G sepharose (Amersham) in lysis buffer was added to the lysate for 30 minutes at 4° C. with mixing. The antibody-bound sepharose was collected by microcentrifugation and washed with 1 ml of lysis buffer three times. The washed sepharose was boiled in 1× sample buffer before being loaded onto a 4-20% SDS-PAGE gel (Pierce). The gel was then transferred overnight to PVDF (Millipore) for blotting.

Expression was confirmed on Western blots using an anti-FLAG M2 monoclonal antibody (Stratagene) at 1:3000 in TBS/1% Casein (Pierce) and chemiluminescent detection (ECL, Amersham) (FIG. 6). A single band of approximately 40 kDa was observed for the total cell lysate preparation. Only the anti-FLAG monoclonal antibody and the polyclonal antisera from LabVision were successful in immunoprecipitating canine CD20 from the total cell lysate (FIG. 6).

Figure 7:
FIG. 7 is an example of a COS7 cell expressing canine CD20 on the surface of the cell as detected by anti-FLAG immunofluoresence and confocal microscopy with three-dimensional reconstruction.

Cellular expression of canine CD20 was also demonstrated using immunofluorescence with the anti-FLAG antibody. COS7 cells transiently transfected with canine CD20, as described above, were grown in two-well chamber slides (Nunc). At 48 hours post-transfection, the cells were washed twice with PBS, and fixed in 4% neutral buffered formalin for 15 minutes. Slides were washed three times in PBS for 5 minutes each, followed by a 15 minute incubation with 50 mM ammonium chloride in PBS. After three five minute washes in PBS, the slides were blocked for 1 hour with PBA (PBS, 0,1% Triton X-100, 15% normal goat serum, 1% BSA). Anti-FLAG M2 antibody (Stratagene) was diluted 1:200 in PBA and added to the slides upon removal of the blocking solution and incubated for 1 hour at room temperature. Slides were washed three times for 5 minutes in PBS before adding a goat anti-mouse FITC conjugated secondary antibody (Jackson ImmunoResearch) at a 1:250 dilution in PBA. The samples were incubated for 1 hour at room temperature and again washed three times for five minutes in PBS. Confocal microscopy was performed to evaluate surface expression of canine CD20. FIG. 7 shows the results of the immunofluorescent labeling and surface expression of canine CD20.

Example 3

Use of Canine CD20 for Peptides:

Based on the amino acid sequence of the canine CD20, and alignment with CD20 proteins from other species, a polypeptide sequence was identified that represents the predominant extracellular domain of the canine CD20 protein. This 53-mer polypeptide was synthesized alone (SEQ ID NO:10; FIG. 8) and in conjunction with a murine T-cell epitope from ovalbumin (SEQ ID NO:11; FIG. 8). The latter polypeptide was conjugated to KLH and BSA and was used to immunize mice in order to generate monoclonal antibodies to the extracellular domain of canine CD20. The former polypeptide was used in an ELISA to screen hybridomas for a monoclonal antibody specific to the extracellular domain of canine CD20.

The peptide ELISA was performed by dissolving 1 mg of the 53-mer peptide (SEQ ID NO: 10) in 1 ml of DMSO (Sigma). Peptide was coated onto 96-well microtiter plates (Immunlon 4HB, Dynatech) at a concentration of 10 ug/ml in 50 mM carbonate (pH 9) overnight at room temperature. Plates were washed four times in PBS-T (phosphate buffered saline (pH 7.2), 0.05% Tween-20) and blocked with 2% Tween-20 in 100 mM Tris (pH7.4) for 2 hours at room temperature. Plates were washed four times in PBS-T before samples were added either neat, for hybridoma supernatants, or diluted in sample diluent (50 mM Tris (pH 7.2), 0.05% Tween-20, 50% fetal bovine serum), for serum samples. Plates were incubated for 1 hour at room temperature, washed four times in PBS-T, and a 1:2500 dilution of goat anti-mouse HRPO (Jackson ImmunoResearch) in sample diluent was added. Following a 1 hour incubation at room temperature, plates were washed six times in PBS-T and developed with at TMB substrate (Moss, Inc.).

Example 4

Production of Monoclonal Antibodies to Canine CD20

Figure 9:
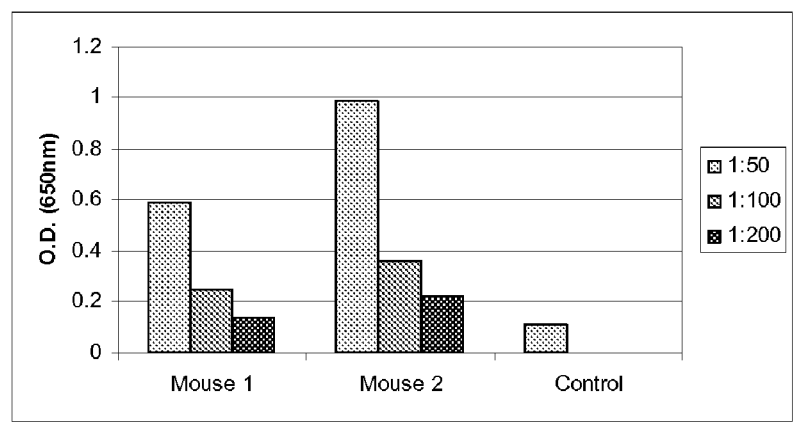
FIG. 9 depicts the serum titers obtained from two mice immunized with canine CD20 as evaluated in the peptide ELISA.

Purified vector DNA (MaxiPrep Kit, Qiagen) containing the canine CD20 gene (Example 2) was used for DNA immunization of mice according to published protocols (Ulmer, J. B. et al. Science, 1993). Antibody titers from individual mice were evaluated ten days after the second immunization using the peptide ELISA described in Example 3. Positive titers were found for each DNA-immunized mouse (FIG. 9). A third injection was performed three weeks after the second injection and the spleen was harvested within 7-10 days for the fusion. The spleen was fused with a mouse myeloma cell line FO using methods well know to those skilled in the art (see Antibodies, a Laboratory Manual, by Harlow and Lane, Cold Spring Harbor Laboratory Press, 1988, pp 139-238). Individual monoclonal antibody producing clones were isolated using the process of limited dilution and screened on the peptide ELISA described in Example 3. A total of 26 clones were isolated from the screening, all of which produced IgM antibodies.

Example 5

Immunocytochemical Evaluation of Monoclonal Antibodies to Canine CD20

The 26 identified clones reactive to the extracellular domain of canine CD20were further evaluated on smears of canine lymph node aspirates using immunocytochemical techniques. Each smear was outlined with an ImmEdge™ hydrophobic barrier pen (Vector Labs), allowed to dry, and then fixed in acetone for 3 minutes. Following a 5 minute wash in PBS (pH 7.2), slides were treated with ammonium chloride (50 mM in PBS) for 15 minutes at room temperature. Following a 5 minute wash in PBS, slides were blocked in PBS/NGS (PBS with 15% normal goat serum (Vector Labs)) for 30 minutes at room temperature. Each hybridoma supernatant was then added to the slide and incubated for one hour at room temperature. Slides were washed twice for 5 minutes in PBS, followed by a 30 minute incubation in a 1:200 dilution of goat anti-mouse IgM +IgG (H+L) F(ab)$_2$ FITC (Jackson ImmunoResearch) in PBS/NGS. Following two 5 minute washes in PBS, slides were examined using fluorescent microscopy. Of the 26 clones initially identified, only five clearly demonstrated immunofluoresence on the lymph node aspirates.

Example 6

Figure 10:
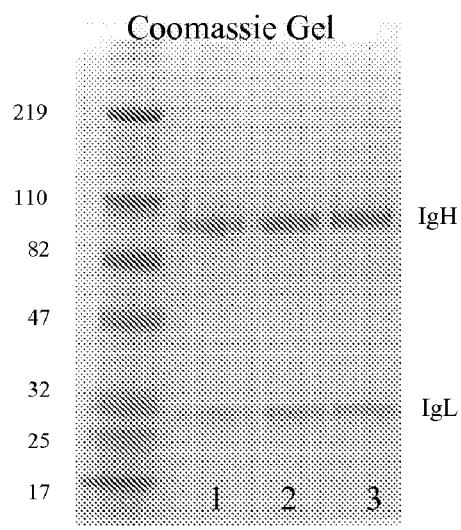
FIG. 10 is a Coomassie stained SDS-PAGE gel showing the purified IgM monoclonal antibodies that recognize the extracellular domain of canine CD20. Monoclonal antibody F3C7 is shown in lane 1, F7A5 is shown in lane 2, and F19 is shown in lane 3.

Flow Cytometric Evaluation of Monoclonal Antibodies to Canine CD20 in Canine Lymphoma Of the five clones identified, four were propagated in 1 L bioreactor bags (VectraCell) according to the manufacturer's instructions using hybridoma serum-free media (Invitrogen). IgM antibodies were purified from the culture supernatants using a HiTrap IgM column (Amersham Biosciences) according to the product insert (FIG. 10). Purified antibodies were conjugated to NHS-Fluoroscein (Sigma/Fluka) by mixing a 20 molar excess of conjugate with the antibody and allowing this to incubate for 30 minutes at room temperature. Antibodies were then purified from unreacted NHS-Fluoroscein using a microspin desalting column (Zeba Spin Column, Pierce) and PBS (pH 7.2).

Of the four antibodies that were fluorescently tagged, only two showed significant labeling of lymphocytes by flow cytometry on lymph node aspirates from dogs with lymphoma. The cell lines secreting these antibodies have been deposited with the ATCC, Manassas Va. on Mar. 30, 2005. Strain designations are F3C7 and F7A5, bearing ATCC Patent Deposit Numbers PTA-6661 and PTA 6662, respectively.

Figure 11:
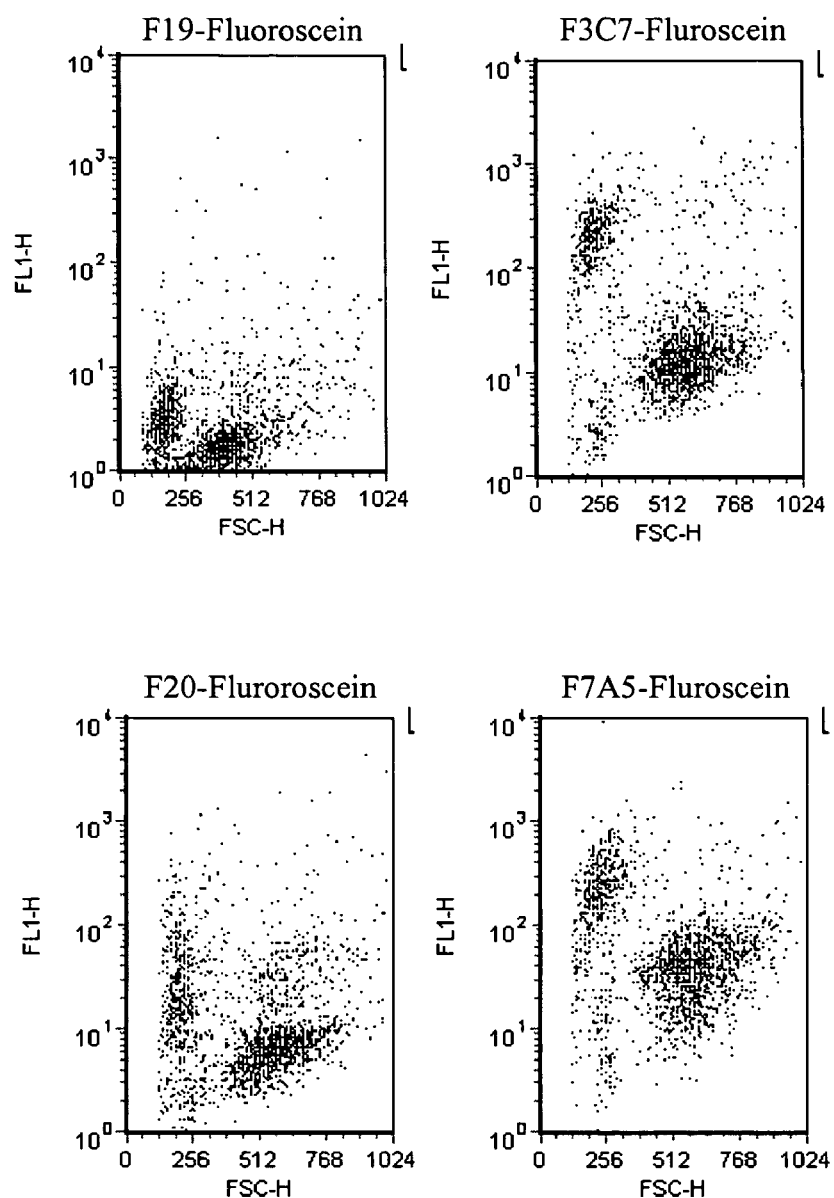
FIG. 11 depicts the flow cytometry results for the four fluorescently labeled IgM monoclonal antibodies to canine CD20 when used to label a lymph node aspirate from dogs with lymphoma.
Figure 12:
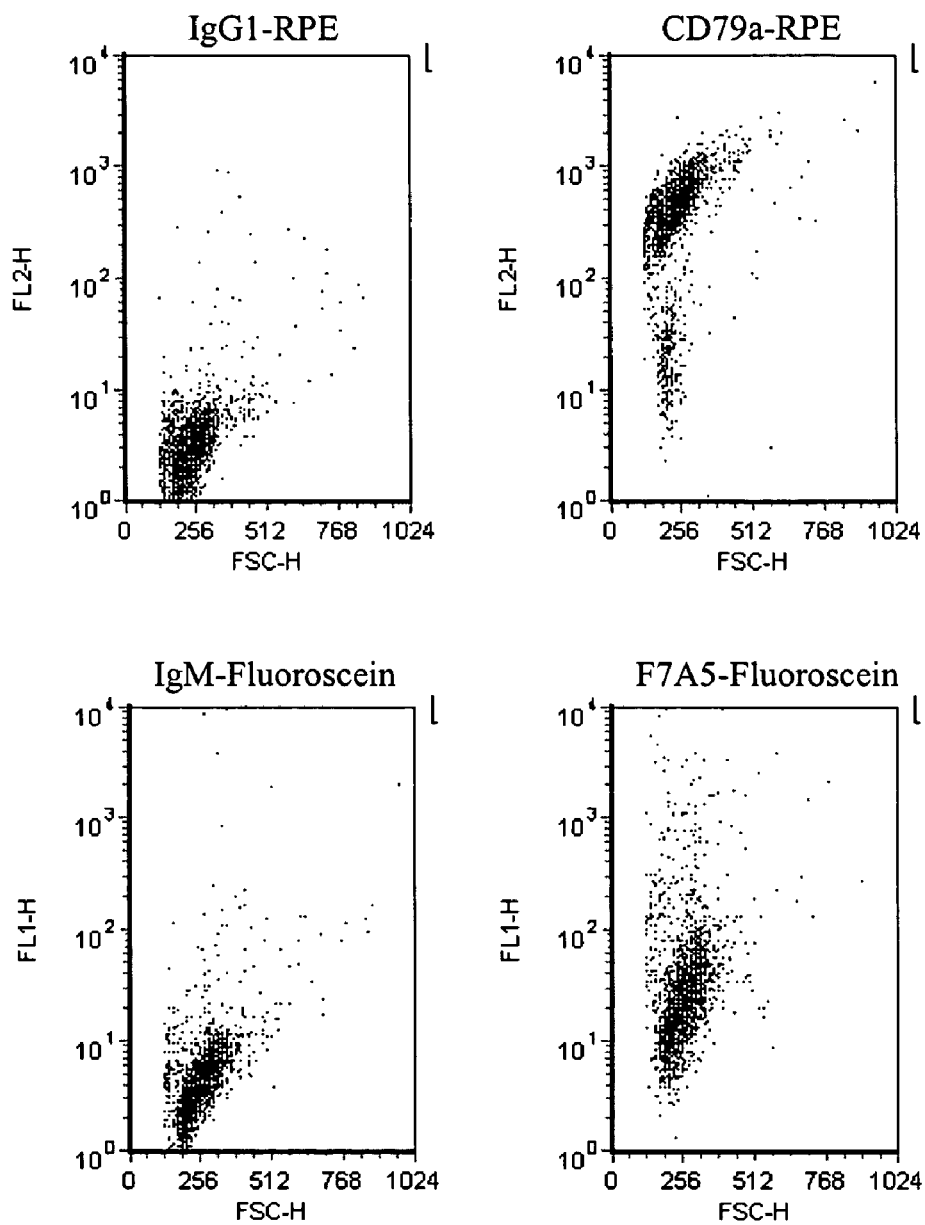
FIG. 12 shows the flow cytometry results for the fluorescently labeled IgM monoclonal antibody F7A5 on a lymph node aspirate from a dog with a B-cell lymphoma. Scatter plots are also shown for an isotype control for the CD20 antibody (IgM-fluorescein), an anti-CD79a B-cell antibody and the corresponding IgG1 isotype control.

For flow cytometry, lymph node aspirates were collected into 1 ml of media (Hanks Balanced Salt Solution (HBSS), 30 mM HEPES, 2% fetal bovine serum, K$_3$EDTA, Pen/Strep) and stored at 4° C. An aliquot of 100 ul was blocked with 25 μg of mouse gamma globulin (Jackson ImmunoResearch) for 20 minutes on ice. The cells were then incubated for 30 minutes on ice with approximately 60 μg of either F3C7 or F7A5. Controls included unlabeled cells, cells labeled with a fluoroscein isotype control, cells labeled for a standard B-cell marker (5 μl anti-CD79a-RPE, DAKOCyotmation) and an RPE isotype control (5 μl IgG1-RPE, DAKOCyotmation). Cells were washed twice with BD Stain Buffer (BD Biosciences) and fixed in BD Cytofix for 15 minutes on ice, followed by two washes in BD Stain Buffer. Labeled cells were analyzed on a Becton Dickinson Flow Cytometer. Representative examples of the anti-canine CD20 monoclonal antibodies labeling B-cell lymphomas are shown in FIGS. 11 and 12.

Example 7

Use of Monoclonal Antibodies to the Extracellular Domain of Canine CD20 in a Point of Care Hematology Instrument to Identify B-Lymphocytes.

Monoclonal antibody F7A5 was labeled with 60 nm colloidal gold (BBInternational). The pH of the gold was initially adjusted to pH 9 with 100 mM K$_2$CO$_3$. The F7A5 monoclonal antibody was diluted to approximately 2 mg/ml in 2 mM borate (pH 9) and was added dropwise to the gold with stirring to a final concentration-of 12 μg/ml. After 15 minutes the gold-antibody solution was stabilized with a 1:10 dilution of 10% BSA (pH 9). After 15 minutes of mixing the gold was centrifuged and washed three times (1% BSA, 1 mM NaCl, pH 9) and resuspended in the wash buffer to a final OD of 5. A lymph node aspirate from the popliteal node of a healthy, young dog was obtained and resuspended in the collection media described in Example 6. A 100 μl aliquot of this sample was incubated with 10 μl of the colloidal gold labeled F7A5 monoclonal antibody to canine CD20 for 30 minutes at room temperature. The sample was then diluted in 0.5 mls of PBS immediately prior to analysis. As a control, an unlabeled aliquot of identical volume from the same aspirate was analyzed in 0.5 ml of PBS.

Samples were analyzed on a point of care hematology instrument (LaserCyte, IDEXX Laboratories, Inc.) under routine conditions, substituting the standard sheath solution for PBS. See, e.g., U.S. Pat. Publ. No. 2004/0246480. Data obtained from the samples was analyzed using standard flow cytometry software (FCS Express 2, De Novo Software). Initially, small lymphocytes are gated in the forward scatter high (FSH) vs time of flight channel (TOF). Medium lymphocytes can be identified in the extinction integral (EXTint) channel vs. TOF. After selecting for each of these populations, the data can be analyzed for degree of right angle scatter, comparing the unlabeled control to the F7A5 labeled sample. Due to the light scattering properties of colloidal gold, cells labeled with the gold-tagged F7A5 antibody demonstrate increased scatter in the right angle scatter channel (RAS). FIG. 13 shows that approximately 33% of small to medium lymphocytes are identified as B-lymphocytes in this normal lymph node aspirate from a dog. This value is consistent with the values obtained using fluorescently labeled antibodies to canine B-cells on standard flow cytometry as reported in the literature (D. Gibson et al., JVIM (2004) 18:710-17).

Example 8

Use of F7A5 Monoclonal Antibody to Identify B-Lymphocytes in a Lymph Node Aspirate from a Cat with Lymphoma.

Figure 14:
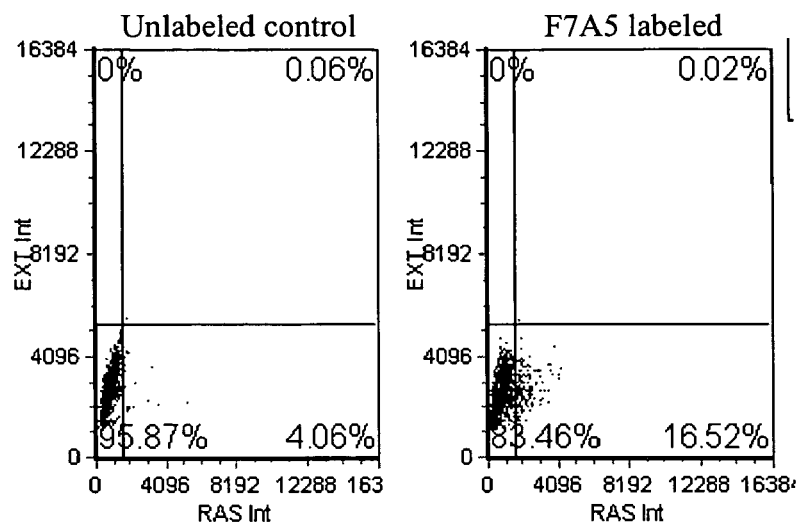
FIG. 14 depicts an example of how the colloidal gold labeled F7A5 monoclonal antibody can be used on a point of care hematology instrument to detect CD20-positive B-lymphocytes in a cat with lymphoma.

A lymph node aspirate from a cat with lymphoma was collected and resuspended in collection media as described in Example 7. A 100 μl aliquot of the sample was labeled with 10 μl of the colloidal gold labeled F7A5 monoclonal antibody for 60 minutes at room temperature. Following labeling the sample was diluted in 1 ml of PBS for analysis as described in Example 7. The lymphocyte populations were determined in a manner similar to that described for Example 7 and the gated lymphocyte population is shown in FIG. 14. Compared to the unlabeled control sample, at least 12.5% of the gated lymphocytes are CD20 positive B-cells.

I claim:

1. An isolated canine CD20 protein comprising the amino acid sequence shown in SEQ ID NO: 6.

2. The isolated protein of claim 1, wherein the protein is present in a fusion protein.

3. An isolated polypeptide comprising the amino acid sequence shown in SEQ ID NO: 10.

4. The isolated polypeptide of claim 3, wherein the polypeptide is present in a fusion protein.

5. An isolated polypeptide, wherein the polypeptide comprises the amino acid sequence shown in SEQ ID NO: 11.

* * * * *